United States Patent
Simard

(10) Patent No.: US 11,370,831 B2
(45) Date of Patent: *Jun. 28, 2022

(54) **COMPOSITIONS AND METHODS FOR TREATING AND PREVENTING *STAPHYLOCOCCUS AUREUS* INFECTIONS**

(71) Applicant: XBIOTECH INC., Vancouver (CA)

(72) Inventor: John Simard, Austin, TX (US)

(73) Assignee: XBIOTECH INC., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/737,841

(22) Filed: Jan. 8, 2020

(65) Prior Publication Data

US 2020/0131252 A1     Apr. 30, 2020

Related U.S. Application Data

(63) Continuation of application No. 16/241,809, filed on Jan. 7, 2019, now Pat. No. 10,577,410, which is a continuation of application No. 15/680,533, filed on Aug. 18, 2017, now Pat. No. 10,214,581, which is a continuation of application No. 15/281,676, filed on Sep. 30, 2016, now Pat. No. 9,783,598, which is a continuation of application No. 15/174,068, filed on Jun. 6, 2016, now Pat. No. 9,486,523, which is a continuation of application No. 14/729,260, filed on Jun. 3, 2015, now Pat. No. 9,416,172.

(60) Provisional application No. 62/115,665, filed on Feb. 13, 2015, provisional application No. 62/041,423, filed on Aug. 25, 2014, provisional application No. 62/007,242, filed on Jun. 3, 2014.

(51) Int. Cl.

| | |
|---|---|
| *A61K 39/40* | (2006.01) |
| *C07K 16/12* | (2006.01) |
| *A61K 38/12* | (2006.01) |
| *A61K 39/085* | (2006.01) |
| *A61K 38/14* | (2006.01) |
| *A61K 39/00* | (2006.01) |

(52) U.S. Cl.
CPC .......... *C07K 16/1271* (2013.01); *A61K 38/12* (2013.01); *A61K 38/14* (2013.01); *A61K 39/40* (2013.01); *A61K 39/085* (2013.01); *A61K 2039/505* (2013.01); *A61K 2300/00* (2013.01); *C07K 2317/21* (2013.01); *C07K 2317/24* (2013.01); *C07K 2317/30* (2013.01); *C07K 2317/34* (2013.01); *C07K 2317/55* (2013.01); *C07K 2317/56* (2013.01); *C07K 2317/565* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 9,416,172 B2* | 8/2016 | Simard | .................. | A61K 38/14 |
| 9,486,523 B2* | 11/2016 | Simard | .................. | A61K 38/12 |
| 9,783,598 B2* | 10/2017 | Simard | .................. | A61K 38/12 |
| 10,214,581 B2* | 2/2019 | Simard | .................. | A61P 31/04 |
| 10,577,410 B2* | 3/2020 | Simard | .................. | A61P 31/04 |

FOREIGN PATENT DOCUMENTS

WO     2008140570     11/2008

OTHER PUBLICATIONS

Kim et al , Infect Immun Oct. 2012; 80(10): 3460-3470. (Year: 2012).*
Wark, Kim L. and Peter J. Hudson: "Latest technologies for the enhancement of antibody affinity," Advanced Drug Delivery Reviews, 2006, No. 58:657-670.
Sela-Culang, I. et al: "The structural basis of antibody-antigen recognition," frontiers in Immunology, Oct. 2013, vol. 4:1-13.

* cited by examiner

*Primary Examiner* — Jennifer E Graser

(74) *Attorney, Agent, or Firm* — Stanley A. Kim

(57) ABSTRACT

Antibodies having Fab regions that specifically bind to *Staphylococcus aureus* protein A are capable of mediating opsinization of *Staphylococcus aureus* bacteria despite their expression of antibody-neutralizing protein A. These antibodies and antigen-binding fragments thereof can be used in methods of treating and/or preventing *Staphylococcus aureus* infections.

2 Claims, 5 Drawing Sheets

Specification includes a Sequence Listing.

COMPOSITIONS AND METHODS FOR TREATING AND PREVENTING *STAPHYLOCOCCUS AUREUS* INFECTIONS

CROSS-REFERENCE TO RELATED APPLICATIONS

This application is a continuation application of U.S. nonprovisional patent application Ser. No. 16/241,809 filed on Jan. 7, 2019, which is a continuation application of U.S. nonprovisional patent application Ser. No. 15/680,533 filed on Aug. 18, 2017 (now U.S. Pat. No. 10,214,581), which is a continuation application of U.S. nonprovisional patent application Ser. No. 15/281,676 filed on Sep. 30, 2016 (now U.S. Pat. No. 9,783,598), which is a continuation application of Ser. No. 15/174,068 filed on Jun. 6, 2016 (now U.S. Pat. No. 9,486,523), which is a continuation application of U.S. nonprovisional patent application Ser. No. 14/729,260 filed on Jun. 3, 2015 (now U.S. Pat. No. 9,416,172), which claims priority from U.S. provisional patent application No. 62/007,242 filed on Jun. 3, 2014, U.S. provisional patent application No. 62/041,423 filed on Aug. 25, 2014, and U.S. provisional patent application No. 62/115,665 filed on Feb. 13, 2015.

SEQUENCE LISTING

The instant application contains a Sequence Listing which has been submitted electronically in ASCII format and is hereby incorporated by reference in its entirety. Said ASCII copy, created on May 28, 2015, is named 5407-0233_SL.txt and is 83,034 bytes in size.

FIELD OF INVENTION

The invention relates generally to methods of medical treatment, immunology, and microbiology. More particularly, the invention relates to compositions and methods for treating and preventing *Staphylococcus aureus* infections.

BACKGROUND

*Staphylococcus aureus* (SA) is a substantial cause of sickness and death in both humans and animals. Infection with these gram-positive cocci often results in the development of a superficial abscess. Other cases of SA infection can be much more serious. For example, intrusion of SA into the lymphatics and blood can lead to a systemic infection which in turn can cause complications such as endocarditis, arthritis, osteomyelitis, pneumonia, septic shock and even death. Hospital-acquired SA infection is common and particularly problematic with SA being the most frequent cause of hospital-acquired surgical site infections and pneumonia, and the second most frequent cause of cardiovascular and bloodstream infections. Antibiotic administration has been and remains the standard treatment for SA infections. Unfortunately, the use of antibiotics has also fueled the development of antibiotic resistance in SA. Notably, methicillin-resistant SA (MRSA) has evolved the ability to resist beta-lactam antibiotics such as penicillin and cephalosporins. More alarmingly, SA resistant to antibiotics of last resort such as vancomycin and linezolid have recently emerged. Therefore a new approach for preventing and treating SA infections is needed

SUMMARY

It was discovered that certain antibodies (Abs) having Fab region paratopes that specifically bind to SA protein A (SpA) are capable of mediating opsinization of SA bacteria despite SA's expression of antibody (Ab)-neutralizing SpA. Previous Ab-based strategies for treating or preventing SA infections showed promise in pre-clinical and early stage clinical trials, but failed to meet endpoints in phase III trials. Perhaps explaining these results, previous strategies did not address the Ab-neutralizing property of SpA. SpA is a heavily expressed cell wall-associated protein that binds most immunoglobulins (Igs) via their Fc (effector) regions. SpA binds to human antibodies of subclasses IgG1, IgG2, and IgG4 via their Fc region with a KD of about $1\times10^{-9}$ M, and thereby acts as an Fc region anchor that orients the effector portion of an immunoglobulin (Ig) away from Fc-interacting immune effectors such as complement and Fc receptor (FcR)-bearing phagocytes. Accordingly, most Abs specific for SA antigens are "sequestered" from immune effectors in this manner. In addition, because SpA is so highly expressed on the cell wall of SA (estimated 7% of the cell wall), it mediates the formation of a shield of Igs covering the cell wall. This shield sterically hinders Abs specific for cell wall antigens from binding their targets and mediating oponophagocytosis of the bacteria. The formation of an Ig shield was not previously appreciated as a virulence factor. Thus the discovery that SA-binding Abs having Fab regions that specifically bind SpA while permitting their Fc regions to still interact with FcRs on immune effector cells and/or activate complement by binding C1q despite the Fc-neutralizing ability of SpA and the formation of an Ig shield was a significant step over other anti-SA Ab-based approaches. Preferred versions of such Abs are capable of displacing Igs already bound to SpA by their Fc regions.

As examples of the foregoing, described herein are isolated or purified antibodies (particularly human IgG3 antibodies which have Fc regions with low or no affinity for SpA such as one with the allotype having arginine at amino acid position 435; Stapleton et al., Nature Communications 2, Article number: 599, 2011) having Fab regions that can specifically bind a target epitope of SpA on a SA bacterium while their Fc regions are still able to interact with an FcR (e.g., soluble recombinant or native on immune effector cells)—despite the Fc-binding property of SpA and steric hindrance of the target epitope by Igs bound to SpA via their Fc region. Also provided herein are pharmaceutical compositions that contain at least one of these antibodies and a pharmaceutically acceptable carrier (e.g., a non-natural pharmaceutically acceptable carrier). Further provided are methods of treating a subject having a SA infection or reducing the risk of developing a SA infection in a subject that include administering a therapeutically effective amount of any of the pharmaceutical compositions described herein or any of the antibodies or antigen-binding fragments described herein to a subject in need thereof.

As used herein, the word "a" or "an" before a noun represents one or more of the particular noun. For example, the phrase "an antibody" represents "one or more antibodies."

By the term "antibody" or "Ab" is meant any immunoglobulin (e.g., human, cartilagenous fish, or camelid antibodies) or conjugate thereof, that specifically binds to an antigen (e.g., an SpA antigen such as SEQ ID NO: 1 or an antigenic fragment of SEQ ID NO: 1). A wide variety of Abs are known by those skilled in the art. Non-limiting examples of Abs include: monoclonal Abs (e.g., including full-length Abs), polyclonal Abs, multi-specific Abs (e.g., bi-specific Abs), dual variable domain Abs, single-chain Abs (e.g., single-domain Abs, camelid Abs, and cartilagenous fish Abs), chimeric (e.g., humanized, such as humanized IgG3)

Abs, and human Abs (e.g., human IgG3 Abs). The term antibody also includes Ab conjugates (e.g., an Ab conjugated to a stabilizing protein, a label, or a therapeutic agent (e.g., any of the therapeutic agents described herein or known in the art)).

By the term "antigen-binding fragment" is meant any portion of a full-length Ab that contains at least one variable domain ((e.g., a variable domain of a mammalian (e.g., human, mouse, rat, rabbit, or goat) heavy or light chain immunoglobulin), a camelid variable antigen-binding domain (VHH), or a cartilagenous fish immunoglobulin new antigen receptor (Ig-NAR) domain) that is capable of specifically binding to an antigen. For example, an antigen-binding fragment described herein can include at least part of an Ab Fc region that is sufficient to mediate antibody-dependent cell-mediated cytotoxicity (ADCC) and/or complement-dependent cytotoxicity (CDC) in a mammal (e.g., a human) and/or is conjugated to a therapeutic agent (e.g., any of the therapeutic agents described herein or known in the art). Non-limiting examples of Ab fragments include Fab, Fab', F(ab')2, Fv fragments, diabodies, linear antibodies, and multi-specific Ab formed from Ab fragments. Additional Ab fragments containing at least one camelid VHH domain or at least one cartilagenous fish Ig-NAR domain include mini-bodies, micro-antibodies, sub-nano-antibodies, and nano-antibodies, and any of the other forms of Abs described in U.S. Patent Application Publication No. 2010/0092470. An antigen binding fragment can be, e.g., an antigen-binding fragment of human or humanized IgG1, IgG2, IgG3 IgG4, IgD, IgA, IgE, or IgM.

By the term "human antibody" is meant an Ab that is encoded by a nucleic acid (e.g., rearranged human immunoglobulin heavy or light chain locus) present in the genome of a human. In some embodiments, a human Ab is produced in a mammalian (e.g., human) cell culture. In some embodiments, a human Ab is produced in a non-human cell (e.g., a Chinese hamster ovary cell line or a mouse or hamster cell line). In some embodiments, a human Ab is produced in a bacterial or yeast cell. A human Ab can include a conjugated therapeutic agent (e.g., any of the therapeutic agents described herein or known in the art). A human Ab can be human IgG1, IgG2, IgG4, IgD, IgA, IgE, or IgM, and is preferably human IgG3. By the term "true human antibody" is meant an Ab with heavy and light chain variable regions that are naturally present in the serum of a human being.

By the term "humanized antibody" is meant an Ab which contains mostly sequences of a human Ab but also includes minimal sequences derived from a non-human (e.g., mouse, rat, rabbit, or goat) Ig. In non-limiting examples, humanized Abs are human Abs (recipient Ab) in which hypervariable region residues of the recipient Ab are replaced by hypervariable region residues from a non-human species Ab (donor Ab), e.g., mouse, rat, rabbit, or goat Ab having the desired specificity, affinity, and capacity. In some embodiments, the Fv framework residues of the human Ig are replaced by corresponding non-human residues. In some embodiments, humanized Abs may contain residues which are not found in the recipient Ab or in the donor Ab. These modifications can be made to further refine Ab performance.

In some embodiments, the humanized Ab will contain substantially all of at least one, and typically two, variable domains, in which all or substantially all of the hypervariable loops (complementary determining regions) correspond to those of a non-human immunoglobulin and all or substantially all of the framework regions are those of a human immunoglobulin sequence. The humanized antibody can also contain at least a portion of an Ig constant region (Fc region), typically, that of a human Ig (e.g., human IgG3). Humanized Abs can be produced by molecular biology methods that are well known in the art. Non-limiting examples of methods for generating humanized Abs are described herein. A humanized antibody can include a conjugated therapeutic agent (e.g., any of the therapeutic agents described herein or known in the art).

By the term "single-chain antibody" is meant a single polypeptide that contains at least one variable binding domain (e.g., a variable domain of a mammalian heavy or light chain Ig, a camelid variable antigen-binding domain (VHH), or a cartilagenous fish (e.g., shark) immunoglobulin new antigen receptor (Ig-NAR) domain) that is capable of specifically binding to an antigen. Non-limiting examples of single-chain Abs are described herein, and are known in the art (see, for example, the antibodies described in U.S. Patent Publication No. 2010/0092470). A single-domain antibody can include a conjugated therapeutic agent (e.g., any of the therapeutic agents described herein or known in the art).

An Ab or antigen-binding fragment thereof "specifically binds" or "binds specifically" to a particular antigen, e.g., SpA (such as an epitope comprising SEQ ID NO: 1 or an antigenic fragment of SEQ ID NO: 1), when it binds to that antigen, but recognizes and binds to a lesser extent (e.g., does not recognize and bind) to other molecules in a sample. In some embodiments, an Ab or an antigen-binding fragment thereof selectively binds to an epitope with an affinity ($K_D$) equal to or less than $1 \times 10^{-10}$ M (e.g., less than $1 \times 10^{-11}$ M or less than $1 \times 10^{-12}$ M) in phosphate buffered saline (e.g., as determined by surface plasmon resonance). The ability of an Ab or antigen-binding fragment to specifically bind a protein epitope may be determined using any of the methods known in the art or those methods described herein.

By the term "complementarity determining region" or "CDR" is meant a region within an Ig (heavy or light chain Ig) that forms part of an antigen-binding site (paratope) in an Ab or antigen-binding fragment thereof. As is known in the art, a heavy chain Ig normally contains three CDRs: CDR1, CDR2, and CDR3, respectively, and a light chain Ig normally contains three CDRs: CDR1, CDR2, and CDR3. In any Ab or antigen-binding fragment thereof, the three CDRs from the heavy chain Ig and the three CDRs from the light chain Ig together form an antigen-binding site in the Ab or antigen-binding fragment thereof. The Kabat Database is one system used in the art to number CDR sequences present in a light chain Ig or a heavy chain Ig.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1:
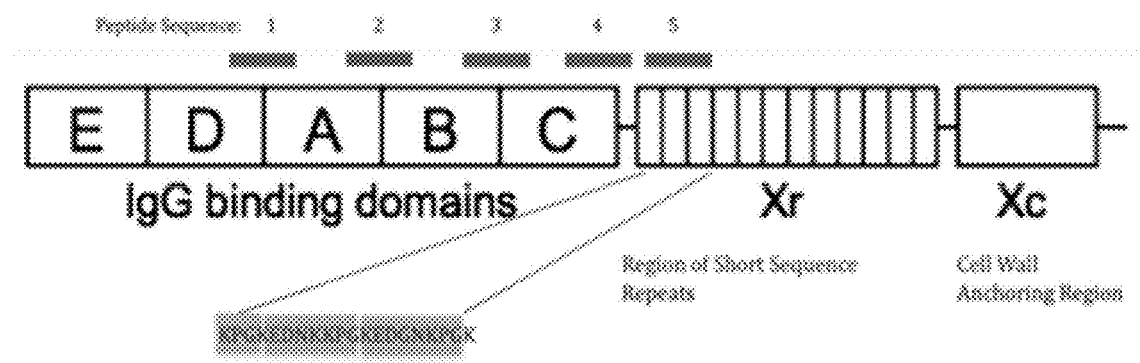
FIG. 1 is a schematic diagram of SpA showing the different domains and the location of each of five antigenic peptides. The sequence of antigenic peptide #5 is shown (SEQ ID NO: 1).
Figure 2:
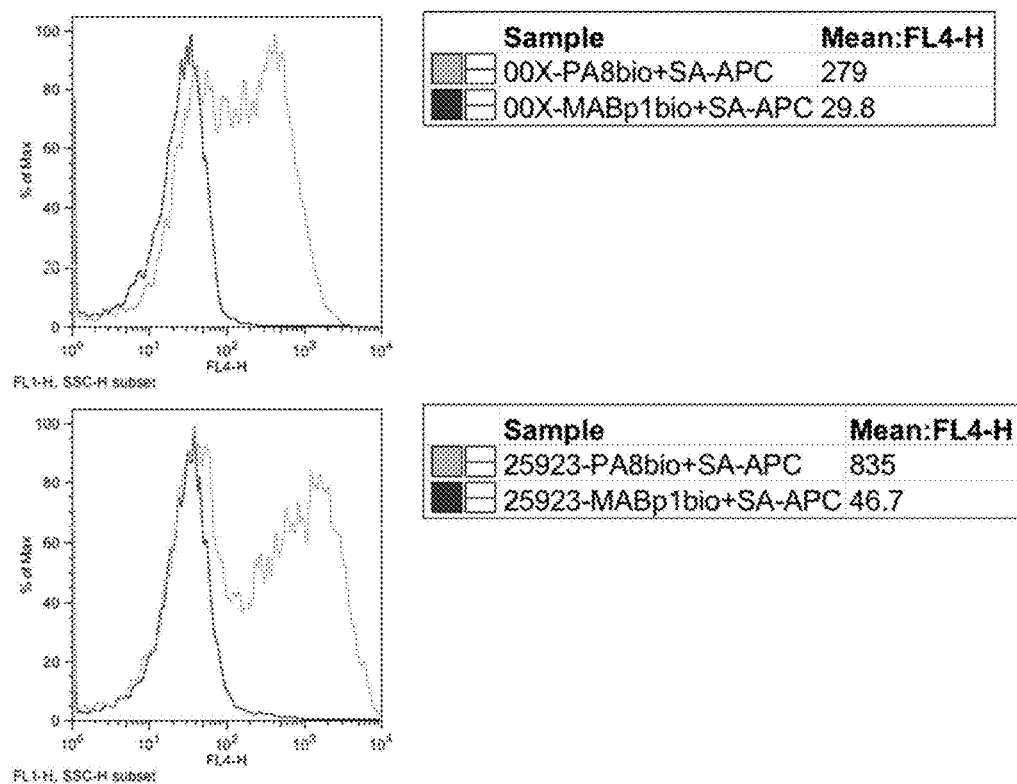
FIG. 2 is a set of two graphs showing a histogram of the fluorescence of SA clinical isolate 00X (top) and SA strain ATCC #25923 (bottom) incubated with biotinylated PA8-G3 Ab (light line) or control biotinylated anti-interleukin-1alpha Ab (MABp1) (dark line), and then incubated with streptavidin-APC.
Figure 3:
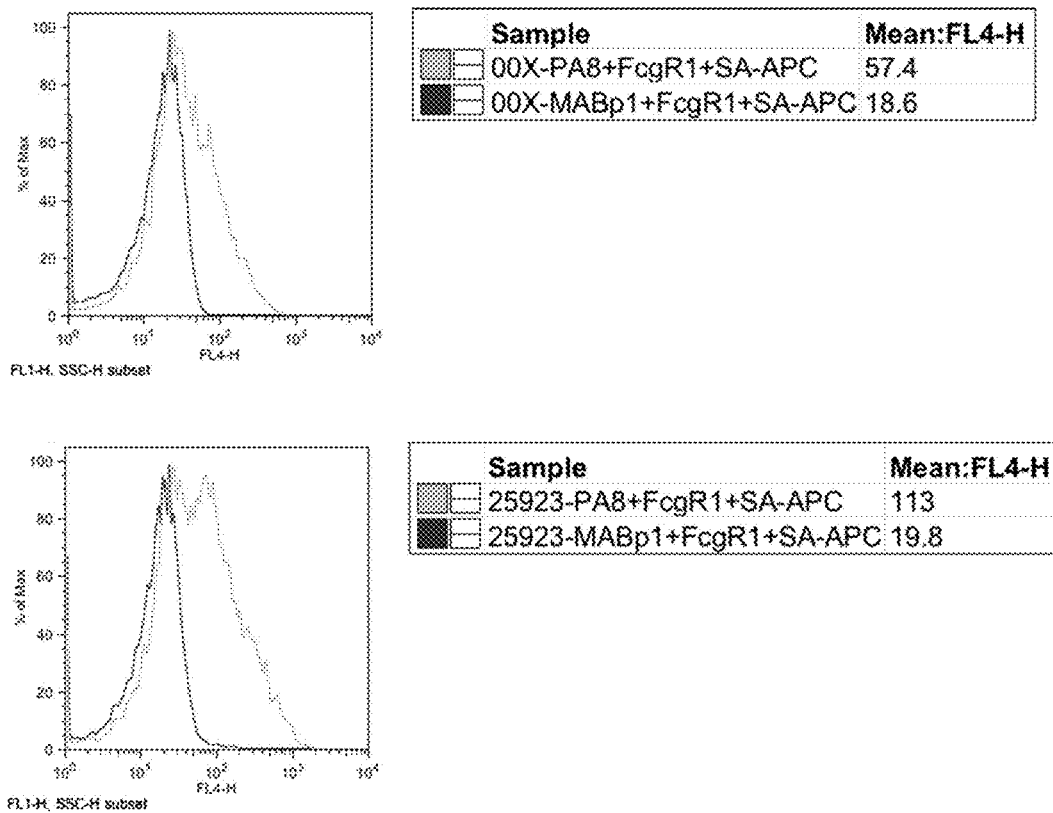
FIG. 3 is a set of two graphs showing a histogram of the fluorescence of clinical isolate 00X (top) and strain ATCC #25923 (bottom) incubated with unlabeled PA8-G3 Ab (light line) or unlabeled MABp1 Ab (dark line), followed by biotinylated recombinant Fcγ receptor 1, and then incubated with streptavidin-APC.
Figure 4:
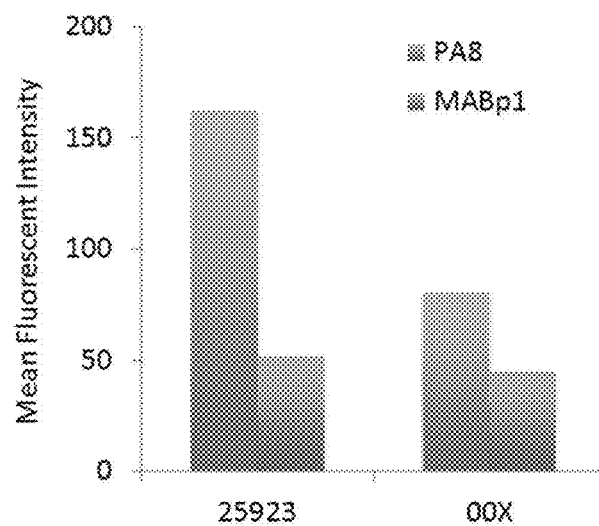
FIG. 4 is graph of the mean fluorescent intensity of differentiated HL60 cells (using fluorescence cell sorting) following co-incubation with PA8-G3 Ab opsonized with pH-rodo-green labeled strain ATCC #25923 or clinical isolate 00X. Similar samples incubated with a control Ab MABp1, instead of PA8-G3 Ab were used as a negative control.

Described herein are methods and compositions for treating a subject having a SA infection or reducing the risk of developing a SA infection in a subject.

Antibodies and Antigen-Binding Fragments Thereof

Described herein are purified or isolated (e.g., at least 90%, 92%, 94%, 95%, 96%, 97%, 98%, or 99% pure by weight) Abs (e.g., preferably true human, human, or humanized IgG3s) that bind to SpA and are capable of mediating opsinization of SA bacteria despite SA's expression of antibody (Ab)-neutralizing SpA. Preferred such Abs bind to the peptide of SEQ ID NO:1 with a sufficient binding affinity to displace human IgG immunoglobulins (e.g., one or more of IgG1, IgG2, and IgG4) bound to SpA via their Fc region. Preferred Abs can bind to SpA via their Fab region paratopes with a $K_D$ of less than $1\times10^{-10}$ M (e.g., less than $1\times10^{-11}$ M, less than $1\times10^{-12}$M, less than $0.5\times10^{-12}$ M, or less than $1\times10^{-13}$M) under physiological conditions (e.g., phosphate buffered saline) (e.g., as determined using surface plasmon resonance or Bio-Layer Interferometry using recombinant SpA). For example, the Abs described herein that bind to SpA via their Fab regions with a $K_D$ of between $1\times10^{-10}$ M and $0.5\times10^{-12}$M, between $1\times10^{-11}$ M and $0.5\times10^{-12}$ M, between $1\times10^{-11}$ M and $0.2\times10^{-12}$ M (e.g., under physiological conditions, e.g., phosphate buffered saline, e.g., as measured used surface plasmon resonance using recombinant SpA) are preferred. Those Abs or antigen-binding fragments described herein preferably are able to displace human Abs (e.g., one or more of IgG1, IgG2, and IgG4) bound to SpA in the cell wall of a SA bacterium via their Fc regions. Also provided herein are purified or isolated (e.g., at least 90%, 92%, 94%, 95%, 96%, 97%, 98%, or 99% pure by weight) mAbs (e.g., preferably true human, human, or humanized IgG3s) that specifically bind Staphylococcus aureus protein A (SpA) with a $K_D$ of less than $1\times10^{-10}$ M via their Fab region paratopes, wherein the mAbs are able to mediate opsinization of SpA-expressing Staphylococcus aureus bacteria in the presence of at least 1 mg/ml (e.g., at least 1, 2, 3, 4, 5, 10, 25, 50, or 100 mg/ml, or the amount normally contained in human serum) of IgG immunoglobulins which bind SpA via their Fc regions The purified or isolated Abs provided herein might bind to an epitope present in the extracellular domain (e.g., present in the $X_R$ repeat region and one or more of the IgG binding domains) of SpA. Non-limiting examples of an antigen that can be specifically recognized by any of the Abs (or antigen-binding fragments thereof) provided herein include: 6, 8, 9, 10, 11, 12, 13, 14, 15, 16, 17, 18, 19, or 20 contiguous amino acids of SEQ ID NO: 1 (e.g., a fragment starting at amino acid position 1, 2, 3, 4, 5, 6, 7, 8, 9, 10, 11, 12, 13, or 14 of SEQ ID NO: 1); 6, 8, 9, 10, 11, 12, 13, 14, 15, 16, 17, 18, 19, 20, or 21 contiguous amino acids of SEQ ID NO: 82 (e.g., a fragment starting at amino acid position 1, 2, 3, 4, 5, 6, 7, 8, 9, 10, 11, 12, 13, 14, or 15 of SEQ ID NO: 82); 6, 7, 8, 9, 10, 11, 12, 13, 14, 15, or 16 contiguous amino acids of SEQ ID NO: 83 (e.g., a fragment starting at amino acid position 1, 2, 3, 4, 5, 6, 7, 8, 9, or 10 of SEQ ID NO: 83); 6, 7, 8, 9, 10, 11, 12, 13, 14, 15, 16, 17, 18, 19, 20, or 21 contiguous amino acids of SEQ ID NO: 84 (e.g., a fragment starting at amino acid position 1, 2, 3, 4, 5, 6, 7, 8, 9, 10, 11, 12, 13, 14, or 15 of SEQ ID NO: 84); 6, 7, 8, 9, 10, 11, 12, 13, 14, 15, 16, 17, 18, 19, or 20 contiguous amino acids of SEQ ID NO: 85 (e.g., a fragment starting at amino acid position 1, 2, 3, 4, 5, 6, 7, 8, 9, 10, 11, 12, 13, or 14 of SEQ ID NO: 85); or 6, 7, 8, 9, 10, 11, 12, 13, 14, 15, 16, 17, 18, 19, or 20 contiguous amino acids from amino acid positions 1 to 20, 10 to 30, 20 to 40, 30 to 50, 40 to 60, 50 to 70, 60 to 80, 70 to 90, 80 to 100, 90 to 110, 100 to 120, 110 to 130, 120 to 140, 130 to 150, 140 to 160, 150 to 170, 160 to 180, 170 to 190, 180 to 200, 190 to 210, 200 to 220, 210 to 230, 220 to 240, 230 to 250, 240 to 260, 250 to 270, 260 to 280, 270 to 290, 280 to 300, 290 to 310, 300 to 320, 310 to 330, 320 to 340, 330 to 350, 340 to 360, 350 to 370, 360 to 380, 370 to 390, 380 to 400, 390 to 410, 400 to 420, 410 to 430, 420 to 440, or 430 or to 450 of SEQ ID NO: 86. Examples of other antigens include similar fragments of SpAs having amino acids sequences differing from that of SEQ ID NO:86.

Methods for determining the ability of an Ab or antigen-binding fragment thereof to bind to a target protein (e.g., SpA or a portion thereof) can be performed using methods known in the art. Non-limiting examples of such methods include competitive binding assays using Abs known to bind the target protein (e.g., SpA), enzyme-linked immunosorbent assays, BioCoRE®, affinity columns, immunoblotting, or protein array technology. In some embodiments, the binding activity of the Ab or antigen-binding fragment thereof is determined by contacting a SA bacterium with the Ab or antigen-binding fragment thereof. Exemplary methods for determining the ability of an Ab or antigen-binding fragment to displace human Abs (e.g., one or more of IgG1, IgG2, and IgG4) bound to SpA in the cell wall of a SA bacterium are described in the Examples section below. Additional methods for determining the ability of an Ab or antigen-binding fragment to displace human Abs (e.g., one or more of IgG1, IgG2, and IgG4) bound to SpA in the cell wall of a SA bacterium are known in the art.

An Ab can be, e.g., a mAb, a multi-specific Ab (e.g., a bispecific Ab), a chimeric Ab (e.g., a humanized Ab, such as a humanized IgG Ab), a human Ab, or a fragment of any of the foregoing. For example, an Ab can be a human or humanized monoclonal IgG3 Ab. An Ab can also be a single-chain Ab (e.g., a single-domain Ab), such as a single-chain camelid or cartilagenous fish (e.g., shark) Ab, or a single-chain Ab that contains at least one camelid variable antigen-binding domain (VHH) or at least one cartilagenous fish (e.g., shark) immunoglobulin new antigen receptor (Ig-NAR) domain (see, for example, the Abs described in U.S. Patent Publication No. 2010/0092470). An Ab can be a whole Ab molecule or an Ab multimer.

The term Ab also includes Ab conjugates (e.g., an Ab conjugated to a stabilizing protein, a label, or a therapeutic agent (e.g., any of the therapeutic agents described herein or known in the art)). An Ab provided herein can, for example, include a Fc domain or part of a Fc domain that is sufficient to mediate Ab-dependent cell-mediated cytotoxicity (ADCC) and/or complement-dependent cytotoxicity (CDC) in a mammal (e.g., a human), and/or is conjugated to a therapeutic agent (e.g., any of the therapeutic agents described herein or known in the art). An Ab can be, e.g., a human or humanized IgG1, IgG2, IgG4, IgD, IgA, IgE, or IgM, and is preferably a human or humanized IgG3.

An antigen-binding fragment described herein can, e.g., include at least part of a Fc domain that is sufficient to mediate Ab-dependent cell-mediated cytotoxicity (ADCC) and/or complement-dependent cytotoxicity (CDC) in a mammal (e.g., a human) and/or is conjugated to a therapeutic agent (e.g., any of the therapeutic agents described herein or known in the art). Non-limiting examples of Ab fragments include Fab, Fab', F(ab')2, single-chain Fvs (scFvs), Fv fragments, fragments containing either a variable light or variable heavy chain domain, diabodies, linear Abs, and multi-specific Abs formed from Ab fragments. Additional Ab fragments containing at least one camelid VHH domain or at least one cartilagenous fish Ig-NAR domain include mini-bodies, micro-Abs, subnano-Abs, and nano-Abs, and any of the other forms of Abs described in U.S. Patent Application Publication No. 2010/0092470.

The Abs or antigen-binding fragments thereof can be of any type (e.g., human or humanized IgG, IgE, IgM, IgD, IgA, and IgY), class (e.g., human or humanized IgG1 (e.g., IgG1a or IgG1b), IgG2 (e.g., IgG2a or IgG2b), IgG3 (e.g., IgG3a or IgG3b), IgG4 (e.g., IgG4a or IgG4b), IgA1, and IgA2 or subclass, although those with an Fc binding affinity for SpA is low (e.g., having a $K_D$ of greater than $1\times10^{-7}$ M, $1\times10^{-6}$ M, $1\times10^{-5}$ M, $1\times10^{-4}$ M, or $1\times10^{-3}$ M; or having a $K_D$ greater than that of SpA for the Fc region of a human IgG1) under physiological conditions (e.g., phosphate buffered saline) (e.g., as determined using surface plasmon resonance using recombinant SpA) are preferred. An antigen binding fragment can be, e.g., an antigen-binding fragment of human or humanized IgG1 (e.g., IgG1a or IgG1b), IgG2 (e.g., IgG2a or IgG2b), IgG4 (e.g., IgG4a or IgG4b), IgD, IgA (e.g., IgA1 or IgA2), IgE, or IgM, and is preferably a fragment of human or humanized IgG3 (e.g., IgG3a or IgG3b). Amino acid mutations may be introduced into the constant region of these IgG subclasses. Amino acid mutations that can be introduced may be, for example, those that enhance binding to Fc receptors (as described in, e.g., *Proc. Natl. Acad. Sci. U.S.A.* 103(11):4005-4010, 2006; MAbs 1(6): 572-579, 2009; US 2010/0196362; US 2013/0108623; US 2014/0171623; US 2014/0093496; and US 2014/0093959), or enhance or decrease binding to FcRn (as described in, e.g., *J. Biol. Chem.* 276(9):6591-6604, 2001; *Int Immunol.* 18(12):1759-1769, 2006; and *J. Biol. Chem.* 281(33):23514-23524, 2006).

Two types of H chains are heterologously associated to produce a bispecific Ab. The knobs-into-holes technology (as described in, e.g., *J. Immunol. Methods* 248(1-2): 7-15, 2001; and *J. Biol. Chem.* 285(27): 20850-20859, 2010), the electrostatic repulsion technology (as described in, e.g., WO 06/106905), the SEEDbody technology (as described in, e.g., *Protein Eng. Des. Sel.* 23(4):195-202, 2010), and such may be used for heterologous association of two types of H chains via a CH3 domain. Any of the antibodies described herein may be those with a modified or deficient sugar chain. Examples of antibodies having modified sugar chains include glycosylation-engineered antibodies (as described in, e.g., WO 99/54342), antibodies with defucosylated sugar chains (as described in, e.g., WO 00/61739, WO 02/31140, WO 06/067847, and WO 06/067913), and antibodies having a sugar chain with bisecting GlcNAc (as described in, e.g., WO 02/79255). Known examples of methods for producing sugar chain-deficient IgG antibodies include the method of introducing a mutation to asparagine at EU numbering position 297 in the heavy chain (*J. Clin. Pharmacol.* 50(5): 494-506, 2010), and the method of producing IgG using *E. coli* (*J. Immunol. Methods* 263(1-2): 133-147, 2002; and *J. Biol. Chem.* 285(27):20850-20859, 2010). Furthermore, heterogeneity accompanying deletion of C-terminal lysine in IgG, and heterogeneity accompanying mispairing of disulfide bonds in the hinge region of IgG2 can be decreased by introducing amino acid deletions/substitutions (as described in, e.g., WO 09/041613). Any of the Abs or antigen-binding fragments described herein includes at least one (e.g., one, two, three, four, five, or six) amino acids (e.g., an added, inserted, or substituted amino acid, e.g., not within a CDR) that are not present in a corresponding human Ab. Any of the Abs or antigen-binding fragments described herein can also have at least one amino acid deleted (e.g., as compared to a corresponding human Ab), e.g., a deletion from the N- or C-terminus of a light or heavy chain, or a deletion of an amino acid from a constant domain (e.g., Fc domain).

SpA, or fragment thereof (e.g., at least 7, 8, 9, or 10 continuous amino acids of SEQ ID NO: 1 (e.g., starting at amino acid position 1, 2, 3, 4, 5, 6, 7, 8, 9, 10, 11, 12, or 13 of SEQ ID NO: 1), or all of SEQ ID NO: 1) can be used as an immunogen to generate Abs using standard techniques for polyclonal and monoclonal Ab preparation. Ab fragments can be generated from monoclonal Abs using well-known methods in the art.

An immunogen typically is used to prepare Abs by immunizing a suitable subject (e.g., rabbit, goat, mouse, or other mammal). An appropriate immunogenic preparation can contain, for example, a recombinantly expressed or a chemically synthesized polypeptide. The preparation can further include an adjuvant, such as Freund's complete or incomplete adjuvant, or a similar immunostimulatory agent.

As an alternative to preparing monoclonal Ab-secreting hybridomas, a monoclonal Ab directed against a polypeptide can be identified and isolated by screening a recombinant combinatorial immunoglobulin library (e.g., an Ab phage display library) with the polypeptide of interest. Kits for generating and screening phage display libraries are commercially available (e.g., the Pharmacia Recombinant Phage Antibody System, Catalog No. 27-9400-01; and the Stratagene SurfZAP* Phage Display Kit, Catalog No. 240612). Additionally, examples of methods and reagents particularly amenable for use in generating and screening an Ab display library can be found in, for example, U.S. Pat. No. 5,223,409; WO 92/18619; WO 91/17271; WO 92/2079; WO 92/15679; WO 93/01288; WO 92/01047; WO 92/09690; WO 90/02809; Fuchs et al., *Bio/Technology* 9:1370-1372, 1991; Hay et al., *Hum. Antibod. Hybridomas* 3:81-85, 1992; Huse et al., *Science* 246:1275-1281, 1989; Griffiths et al., *EMBO J.* 12:725-734, 1993.

Additional methods for isolating and sequencing a human Ab (e.g., human IgG3) that binds specifically to a SpA epitope (e.g., an epitope located or defined within the polypeptide of SEQ ID NO: 1) are described in the Examples section below. Additional general methods for making Abs and antigen-binding fragments are described in U.S. Patent Application Publication No. 2011/0059085.

In some embodiments, Abs or antigen-binding fragments provided herein are human or humanized Abs (e.g., human or humanized IgG3 Abs). In some embodiments, a humanized Ab is a human Ab that has been engineered to contain at least one complementary determining region (CDR) present in a non-human Ab (e.g., a rat, mouse, rabbit, or goat Ab). In some embodiments, a humanized Ab or fragment thereof can contain all three CDRs of a light chain of a human or non-human Ab that specifically binds to a SpA epitope (e.g., an epitope located or defined within the polypeptide of SEQ ID NO: 1). In some embodiments, the humanized Ab or fragment thereof can contain all three CDRs of a heavy chain of a human or non-human Ab that specifically binds to a SpA epitope (e.g., an epitope located or defined within the polypeptide of SEQ ID NO: 1). In some embodiments, the humanized Ab or fragment thereof can contain all three CDRs of a heavy chain and all three CDRs of a light chain of a non-human or human monoclonal Ab that specifically binds to a SpA epitope (e.g., an epitope located or defined within the polypeptide of SEQ ID NO: 1).

Abs of the invention may also include multimeric forms of Abs. For example, Abs of the invention may take the form of Ab dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers within an Ab multimer may be identical or different, i.e., they may be heteromeric or homomeric Ab multimers. For example, individual Abs within a multimer may have the same or different binding specificities.

Multimerization of Abs may be accomplished through natural aggregation of Abs or through chemical or recombinant linking techniques known in the art. For example, some percentage of purified Ab preparations (e.g., purified IgG1 molecules) spontaneously form protein aggregates containing Ab homodimers and other higher-order Ab multimers. Alternatively, Ab homodimers may be formed through chemical linkage techniques known in the art. For example, heterobifunctional crosslinking agents including, but not limited to, SMCC (succinimidyl 4-(maleimidomethyl)cyclohexane-1-carboxylate) and SATA (N-succinimidyl S-acethylthio-acetate) (available, for example, from Pierce Biotechnology, Inc. (Rockford, Ill.)) can be used to form Ab multimers. An exemplary protocol for the formation of Ab homodimers is given in Ghetie et al. (*Proc. Natl. Acad. Sci. U.S.A.* 94: 7509-7514, 1997). Ab homodimers can be converted to Fab'2 homodimers through digestion with pepsin. Another way to form Ab homodimers is through the use of the autophilic T15 peptide described in Zhao et al. (*J. Immunol.* 25:396-404, 2002).

Alternatively, Abs can be made to multimerize through recombinant DNA techniques. IgM and IgA naturally form Ab multimers through the interaction with the mature J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules (see, for example, Chintalacharuvu et al., *Clin. Immunol.* 101:21-31, 2001, and Frigerio et al., *Plant Physiol.* 123:1483-1494, 2000). IgA dimers are naturally secreted into the lumen of mucosa-lined organs. This secretion is mediated through interaction of the J chain with the polymeric IgA receptor (pIgR) on epithelial cells. If secretion of an IgA form of an Ab (or of an Ab engineered to contain a J chain interaction domain) is not desired, it can be greatly reduced by expressing the Ab molecule in association with a mutant J chain that does not interact well with pIgR (Johansen et al., *J. Immunol.*, 167:5185-192, 2001). ScFv dimers can also be formed through recombinant techniques known in the art; an example of the construction of scFv dimers is given in Goel et al. (*Cancer Res.* 60:6964-71, 2000). Ab multimers may be purified using any suitable method known in the art, including, but not limited to, size exclusion chromatography.

Any of the Abs or antigen-binding fragments described herein may be conjugated to a stabilizing molecule (e.g., a molecule that increases the half-life of the Ab or antigen-binding fragment thereof in a feline or in solution). Non-limiting examples of stabilizing molecules include: a polymer (e.g., a polyethylene glycol) or a protein (e.g., serum albumin, such as feline serum albumin). Any of the Abs or antigen-binding fragments described herein may be conjugated to a label (e.g., a fluorophore, radioisotope, or luminescent molecule) or a therapeutic agent (e.g., a cytotoxic agent or a radioisotope). Exemplary methods for attaching a label or therapeutic agent to an Ab are described in U.S. Patent Application No. 2013/0224228. Non-limiting examples of cytotoxic agents include agent known to induce cell death of microbe (e.g., a gram positive bacterium, such as *Staphylococcus aureus*). Non-limiting examples of cytotoxic agents that can be conjugated to any of the Abs or antigen-binding fragments provided herein include: linezolid, erythromycin, mupirocin, ertapenem, doripenem, imipenem, cilastatin, meropenem, cefadroxil, cefazolin, cefalotin, cephalothin, cephalexin, ceflacor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, ceftaroline fosamil, ceftobiprole, teicoplanin, vancomycin, televancin, clindamycin, lincomycin, daptomycin, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sufamethizole, sulfamethoxazole, sulfanilamide, sulfasalazine, sulfisoxazole, trimethoprim-sulfamethoxazole, sulfonamidochrysoidine, demeclocycline, doxycycline, minocycline, oxytetracycline, and tetracycline.

For example, an Ab (e.g., a human or humanized monoclonal IgG3) or antigen-binding fragment thereof (e.g., a fragment of a human or humanized monoclonal IgG3) provided herein that specifically binds to SpA can include:

(i) a heavy chain comprising a CDR1, CDR2, and CDR3 of SEQ ID NOs: 2, 3, and 4, respectively, and/or a light chain comprising a CDR1, CDR2, and CDR3 of SEQ ID NOs: 7, 8, and 9, respectively;

(ii) a heavy chain comprising a CDR1, CDR2, and CDR3 of SEQ ID NOs: 12, 13, and 14, respectively, and/or a light chain comprising a CDR1, CDR2, and CDR3 of SEQ ID NOs: 17, 18, and 19, respectively;

(iii) a heavy chain comprising a CDR1, CDR2, and CDR3 of SEQ ID NOs: 22, 23, and 24, respectively, and/or a light chain comprising a CDR1, CDR2, and CDR3 of SEQ ID NOs: 27, 28, and 29, respectively;

(iv) a heavy chain comprising a CDR1, CDR2, and CDR3 of SEQ ID NOs: 32, 33, and 34, respectively, and/or a light chain comprising a CDR1, CDR2, and CDR3 of SEQ ID NOs: 37, 38, and 39, respectively;

(v) a heavy chain comprising a CDR1, CDR2, and CDR3 of SEQ ID NOs: 42, 43, and 44, respectively, and/or a light chain comprising a CDR1, CDR2, and CDR3 of SEQ ID NOs: 47, 48, and 49, respectively;

(vi) a heavy chain comprising a CDR1, CDR2, and CDR3 of SEQ ID NOs: 52, 53, and 54, respectively, and/or a light chain comprising a CDR1, CDR2, and CDR3 of SEQ ID NOs: 57, 58, and 59, respectively;

(vii) a heavy chain comprising a CDR1, CDR2, and CDR3 of SEQ ID NOs: 62, 63, and 64, respectively, and/or a light chain comprising a CDR1, CDR2, and CDR3 of SEQ ID NOs: 67, 68, and 69, respectively; or (viii) a heavy chain comprising a CDR1, CDR2, and CDR3 of SEQ ID NOs: 72, 73, and 74, respectively, and/or a light chain comprising a CDR1, CDR2, and CDR3 of SEQ ID NOs: 77, 78, and 79, respectively.

In some examples, any of the Abs provided herein has: an Ab heavy chain including SEQ ID NO: 6 and/or a light chain including SEQ ID NO: 11; an Ab heavy chain including SEQ ID NO: 16 and/or a light chain including SEQ ID NO: 21; an Ab heavy chain including SEQ ID NO: 26 and/or a light chain including SEQ ID NO: 31; an Ab heavy chain including SEQ ID NO: 36 and/or a light chain including SEQ ID NO: 41; an Ab heavy chain including SEQ ID NO: 46 and/or a light chain including SEQ ID NO: 51; an Ab heavy chain including SEQ ID NO: 56 and/or a light chain including SEQ ID NO: 61; an Ab heavy chain including SEQ ID NO: 66 and/or a light chain including SEQ ID NO: 71; or an Ab heavy chain including SEQ ID NO: 76 and/or a light chain including SEQ ID NO: 81.

In additional examples, any of the Abs (e.g., a human or humanized IgG3) or antigen-binding fragments (e.g., an antigen-binding fragment of a human or humanized IgG3) provided herein might bind to SpA with a $K_D$ of less than $1 \times 10^{-10}$ M (e.g., less than $1 \times 10^{-11}$ M or less than $1 \times 10^{-12}$ M) and/or be capable of displacing human Abs (e.g., one or more of IgG1, IgG2, and IgG4) bound to SpA, where the antigen or antigen-binding fragment has a set of six CDRs has no more than one, two, three, four, five, or six total amino acid substitutions (e.g., conservative amino acid substitutions) in the set (the entire set) of six CDRs selected from the group consisting of:

(i) SEQ ID NOs: 2, 3, 4, 7, 8, and 9;
(ii) SEQ ID NOs: 12, 13, 14, 17, 18, and 19;
(iii) SEQ ID NOs: 22, 23, 24, 27, 28, and 29;
(iv) SEQ ID NOs: 32, 33, 34, 37, 38, and 39;
(v) SEQ ID NOs: 42, 43, 44, 47, 48, and 49;
(vi) SEQ ID NOs: 52, 53, 54, 57, 58, and 59;
(vii) SEQ ID NOs: 62, 63, 64, 67, 68, and 69; or
(viii) SEQ ID NOs: 72, 73, 74, 77, 78, and 79.

For example, an Ab (e.g., a human or humanized IgG3) or an antigen-binding fragment (e.g., an antigen-binding fragment of a human or humanized IgG3) provided herein can include a set of six CDRs that has no more than one, two, three, or four total amino acid substitutions in the set (the entire set) of six CDRs of SEQ ID NOs: 2, 3, 4, 7, 8, and 9. For example, an Ab (e.g., a human or humanized IgG3) or antigen-binding fragment (e.g., an antigen binding fragment of a human or humanized IgG3) provided herein can comprise or consist of:

(i) a set of six CDRs of SEQ ID NOs: 2, 3, 4, 7, 8, and 9;
(ii) a set of six CDRs of SEQ ID NOs: 12, 13, 14, 17, 18, and 19;
(iii) a set of six CDRs of SEQ ID NOs: 22, 23, 24, 27, 28, and 29;
(iv) a set of six CDRs of SEQ ID NOs: 32, 33, 34, 37, 38, and 39;
(v) a set of six CDRs of SEQ ID NOs: 42, 43, 44, 47, 48, and 49;
(vi) a set of six CDRs of SEQ ID NOs: 52, 53, 54, 57, 58, and 59;
(vii) a set of six CDRs of SEQ ID NOs: 62, 63, 64, 67, 68, and 69; or
(viii) a set of six CDRs of SEQ ID NOs: 72, 73, 74, 77, 78, and 79.

In additional examples, an Ab (e.g., a human or humanized monoclonal IgG3) or antigen-binding fragment (e.g., an antigen-binding fragment of a human or humanized IgG3) provided herein that specifically binds to SpA includes a variable domain selected from the group of: (i) a variable domain comprising or consisting of SEQ ID NO: 5; (ii) a variable domain comprising or consisting of SEQ ID NO: 10; (iii) a variable domain comprising or consisting of SEQ ID NO: 15; (iv) a variable domain comprising or consisting of SEQ ID NO: 20; (v) a variable domain comprising or consisting of SEQ ID NO: 25; (vi) a variable domain comprising or consisting of SEQ ID NO: 30; (vii) a variable domain comprising or consisting of SEQ ID NO: 35; (viii) a variable domain comprising or consisting of SEQ ID NO: 40; (ix) a variable domain comprising or consisting of SEQ ID NO: 45; (x) a variable domain comprising or consisting of SEQ ID NO: 50; (xi) a variable domain comprising or consisting of SEQ ID NO: 55; (xii) a variable domain comprising or consisting of SEQ ID NO: 60; (xiii) a variable domain comprising or consisting of SEQ ID NO: 65; (xiv) a variable domain comprising or consisting of SEQ ID NO: 70; (xv) a variable domain comprising or consisting of SEQ ID NO: 75; or (xvi) a variable domain comprising or consisting of SEQ ID NO: 80. For example, an Ab (e.g., a human or humanized monoclonal IgG3) or antigen-binding fragment (e.g., an antigen-binding fragment of a human or humanized IgG3) can include (i) a variable domain comprising or consisting of SEQ ID NO: 5 and/or a variable domain comprising or consisting of SEQ ID NO: 10; (ii) a variable domain comprising or consisting of SEQ ID NO:15 and/or a variable domain comprising or consisting of SEQ ID NO: 20; (iii) a variable domain comprising or consisting of SEQ ID NO: 25 and/or a variable domain comprising or consisting of SEQ ID NO: 30; (iv) a variable domain comprising or consisting of SEQ ID NO: 35 and/or a variable domain comprising or consisting of SEQ ID NO: 40; (v) a variable domain comprising or consisting of SEQ ID NO: 45 and/or a variable domain comprising or consisting of SEQ ID NO: 50; (vi) a variable domain comprising or consisting of SEQ ID NO: 55 and/or a variable domain comprising or consisting of SEQ ID NO: 60; (vii) a variable domain comprising or consisting of SEQ ID NO: 65 and/or a variable domain comprising or consisting of SEQ ID NO: 70; or a variable domain comprising or consisting of SEQ ID NO: 75 and/or a variable domain comprising or consisting of SEQ ID NO: 80.

Some embodiments of any of the Abs (e.g., human or humanized monoclonal IgG3) or antigen-binding fragments (e.g., an antigen-binding fragment of a human or humanized IgG3) described herein have one or more (e.g., one, two, three, or four) of the following activities: specifically bind to SpA in a strain of MRSA; specifically bind to an epitope defined by SEQ ID NO: 1; bind to SpA with a $K_D$ of less than $1 \times 10^{-10}$ M (e.g., less than $1 \times 10^{-11}$ M or less than $1 \times 10^{-12}$); and displace human Abs bound to SpA in the cell wall of a *Staphylococcus aureus* bacterium (e.g., a MRSA bacterium).

Pharmaceutical Compositions

Provided herein are pharmaceutical compositions containing at least one pharmaceutically acceptable carrier (e.g., a non-natural pharmaceutically acceptable carrier) and at least one (e.g., two, three, or four) of any of the Abs or antigen-binding fragments provided herein. Non-limiting examples of pharmaceutically acceptable carriers include sterilized water, physiological saline, stabilizers, excipients, antioxidants (e.g., ascorbic acid), buffers (e.g., phosphate, citrate, histidine, and other organic acids), antiseptics, surfactants (e.g., PEG and Tween), chelating agents (e.g., EDTA or EGTA), and binders. Additional examples of pharmaceutically acceptable carriers also include low-molecular-weight polypeptides, proteins (e.g., serum albumin and gelatin), amino acids (e.g., glycine, glutamine, asparagine, glutamic acid, aspargic acid, methionine, arginine, and lysine), sugars and carbohydrates (e.g., polysaccharides and monosaccharides), and sugar alcohols (e.g., mannitol and sorbitol). When preparing an aqueous solution for injection, physiological saline and isotonic solutions comprising glucose and other adjuvants such as D-sorbitol, D-mannose, D-mannitol, and sodium chloride may be used, and if necessary, in combination with appropriate solubilizers, such as alcohol (e.g., ethanol), polyalcohols (e.g., propylene glycol and PEG), and nonionic surfactants (e.g., polysorbate 80, polysorbate 20, poloxamer 188, and HCO-50). By mixing hyaluronidase into the formulation, a larger fluid volume can be administered subcutaneously (see, e.g., *Expert. Opin. Drug. Deliv.* 4(4): 427-440, 2007).

The Abs and antigen-binding fragments provided herein may, e.g., be encapsulated in microcapsules (e.g., those made of hydroxymethylcellulose, gelatin, and poly(methylmetacrylate)), or incorporated as components of colloidal drug delivery systems (e.g., liposomes, albumin microspheres, microemulsion, nanoparticles, and nanocapsules) (see, for example, "Remington's Pharmaceutical Science 16th edition", Oslo Ed. (1980)). Methods for preparing the pharmaceutical compositions as controlled-release pharmaceutical agents are also well-known, and such methods may be applied to the Abs and antigen-binding fragments of the present invention (see, e.g., Langer et al., *J. Biomed. Mater. Res.* 15: 267-277, 1981; Langer, *Chemtech.* 12: 98-105, 1982; U.S. Pat. No. 3,773,919; European Patent Application Publication No. EP 58,481; Sidman et al., *Biopolymers* 22: 547-556, 1983; and EP 133,988).

The pharmaceutical compositions provided herein can be formulated for intravenous, intaarterial, intradermally, subcutaneous, intramuscular, intraperitoneal, or oral administration.

The dose of a pharmaceutical composition of the present invention may be appropriately determined by considering the dosage form, method of administration, patient age and body weight, symptoms of the patient, severity of the SA infection, or level of risk of SA infection. Generally, the daily dose for an adult can be, e.g., between 0.1 mg to 10,000 mg at once or in several portions. The dose can be, e.g., 0.2 to 10,000 mg/day (e.g., 1-10 g/day, 2-8 g/day, 1-5 g/day, 0.5 to 2.5 g/day, 0.5 to 500 mg/day, 1 to 300 mg/day, 3 to 100 mg/day, or 5 to 50 mg/day). These doses may vary, depending on the patient body weight and age, and the method of administration; however, selection of suitable dosage is well within the purview of those skilled in the art. Similarly, the dosing period may be appropriately determined depending on the therapeutic progress.

Any of the pharmaceutical compositions provided herein can further include one or more additional antimicrobial agents. Non-limiting examples of such antimicrobial agents include: linezolid, erythromycin, mupirocin, ertapenem, doripenem, imipenem, cilastatin, meropenem, cefadroxil, cefazolin, cefalotin, cefalothin, cephalexin, ceflacor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, ceftaroline fosamil, ceftobiprole, teicoplanin, vancomycin, televancin, clindamycin, lincomycin, daptomycin, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sufamethizole, sulfamethoxazole, sulfanilamide, sulfasalazine, sulfisoxazole, trimethoprim-sulfamethoxazole, sulfonamidochrysoidine, demeclocycline, doxycycline, minocycline, oxytetracycline, and tetracycline.

Methods of Treating a Subject Having a *S. aureus* Infection or Reducing the Risk of Developing a *S. aureus* Infection in a Subject Also provided are methods of treating a subject having a SA infection (e.g., MRSA infection, SA bacteremia, SA skin infection, SA mastitis, SA cellulitis or folliculitis, or SA-involved wound infections, abscesses, osteomyelitis, endocarditis, pneumonia, septic shock, food poisoning, or toxic shock syndrome) that include administering to a subject (e.g., a human being or another mammal such as a bovine, ovine, canine, feline, equine, hircine, leporine, porcine, or avian) in need thereof a therapeutically effective amount of at least one of any of the pharmaceutical compositions provided herein or at least one of any of the Abs or antigen-binding fragments provided herein. In some examples, the subject has been diagnosed or identified as having a SA infection (e.g., a MRSA infection). Some embodiments further include (prior to the administering step) a step of diagnosing, identifying, or selecting subject having or as having a SA infection (e.g., a MRSA or VRSA infection). In some examples, the SA infection is a nosocomial infection. In some examples, the subject has previously been treated with an antibacterial treatment and the prior treatment was unsuccessful.

Also provided are methods of reducing a subject's risk of developing a SA infection (e.g., a MRSA infection) that include administering to the subject an effective amount of at least one of any of the pharmaceutical compositions provided herein or at least one of any of the Abs or antigen-binding fragments provided herein. In some embodiments, the SA infection is a nosocomial infection. Some embodiments further include prior to administering selecting or identifying a subject as having an increased risk of developing a SA infection (e.g., a MRSA infection). For example, the subject can be a medical professional (e.g., a physician, a nurse, a laboratory technician, or a physician's assistant) (e.g., a medical professional in physical contact with a subject having a SA infection (e.g., a MRSA infection)). A subject in these methods can also be a subject admitted to a hospital or inpatient treatment (e.g., a nursing home) that contains (has admitted) at least one other subject having a SA infection (e.g., a MRSA infection). The subject may be a hospitalized patient such as one in the intensive care unit, an immunocompromised patient, and a patient who has undergone or will undergo a surgical procedure (e.g, cardiac surgery).

In any of the methods provided herein, the subject can be a male or a female. For example, the subject can an infant, a toddler, an adolescent, a teenager, or an adult (e.g., at least 18 years old, at least 20 years old, at least 25 years old, at least 30 years old, at least 35 years old, at least 40 years old, at least 45 years old, at least 50 years old, at least 55 years old, at least 60 years old, at least 65 years old, at least 70 years old, at least 75 years old, at least 80 years old, at least 85 years old, at least 90 years old, at least 95 years old, or at least 100 years old). In some examples, the subject has a suppressed or weakened immune system (e.g., humoral or cellular immune system).

In some examples, the at least one pharmaceutical composition provided herein or at least one Ab or antigen-binding fragment provided herein is administered by intravenous, intaarterial, intradermally, subcutaneous, intramuscular, intraperitoneal, or oral administration. For example, in methods of reducing the risk of developing a SA infection, the subject is administered at least one of the pharmaceutical compositions provided herein or at least one of the Abs or antigen-binding fragments provided herein prior to or shortly after coming into physical contact with a subject identified, diagnosed, having, or suspected of having SA infection (e.g., a MRSA infection).

In any of the methods described herein, the subject is administered at least one (e.g., two, three, four, five, six, seven, eight, nine, or ten) dose(s) of any of the pharmaceutical compositions provided herein or at least one (e.g., two, three, four, five, six, seven, eight, nine, or ten) dose(s) of any of the Abs or antigen-binding fragments provided herein. A subject can be administered two of more doses of any of the pharmaceutical compositions or at least two doses of any of the Abs or antigen-binding fragments provided herein at a frequency of at least one dose every month (e.g., at least two doses every month, at least three doses every month, at least four doses every month, at least one dose a week, at least two doses a week, at least three doses a week, at least four doses a week, at least five doses a week, at least one dose a day, at least two doses a day, or at least three doses a day).

Some embodiments further include co-administering to a subject and Ab described herein and one or more additional antimicrobial agents. Non-limiting examples of such antimicrobial agents include: linezolid, erythromycin, mupirocin, ertapenem, doripenem, imipenem, cilastatin, meropenem, cefadroxil, cefazolin, cefalotin, cefalothin, cephalexin, ceflacor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, ceftaroline fosamil, ceftobiprole, teicoplanin, vancomycin, televancin, clindamycin, lincomycin, daptomycin, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sufamethizole, sulfamethoxazole, sulfanilamide, sulfasalazine, sulfisoxazole, trimethoprim-sulfamethoxazole, sulfonamidochrysoidine, demeclocycline, doxycycline, minocycline, oxytetracycline, and tetracycline. Additional examples of therapeutic agents that can be included in any of the pharmaceutical compositions provided herein are one or more Abs described in U.S. Patent Application Publication No. 2011/0059085.

Kits

Also provided herein are kits containing at least one (e.g., two, three, four, or five) of any of the Abs or antigen-binding fragments provided herein. In some examples, the kits can contain a recombinant SpA or a peptide comprising or consisting of SEQ ID NO: 1 or an antigenic fragment of SEQ ID NO: 1 (e.g., at least 7 continguous amino acids of SEQ ID NO: 1 (e.g., starting at amino acids position 1, 2, 3, 4, 5, 6, 7, 8, 9, 10, 11, 12, or 13 of SEQ ID NO: 1)). In some examples, the at least one Ab or antigen-binding fragment is attached to a solid substrate (e.g., a well, a chip, a film, a bead, or a chromatography resin). Such kits can include commercial packaging and/or printed information about the Abs and methods of their use.

EXAMPLES

Example 1

Generation of Human Abs that Specifically Bind to SpA and Displace Human IgG Immunoglobulins Bound to SpA Via their Fc Region Human IgG3 Abs that bind to a SpA epitope were generated as described below. Five synthesized peptides covering the IgG-binding and Xr repeat sequences in SpA were used to screen for anti-peptide Abs in the blood of 311 healthy adult volunteers. The five synthesized peptides from SpA used for screening had the sequences indicated as: SEQ ID NOs: 82, 83, 84, 85, and 1 (peptides 1, 2, 3, 4, and 5, respectively). About 4% of the healthy subjects had greater than 10-fold higher levels of anti-peptide (anti-SpA) Abs over background (hereafter called "positive donors") as determined using an enzyme-linked immunosorbent assay (ELISA). Plasma from these positive donors was obtained and used to isolate true human Abs that bind specifically to a peptide covering the IgG-binding and Xr repeat sequences of SpA using the methods described in U.S. Patent Application Publication No. 2013/0018173. In sum, Abs of interest were isolated using antigen affinity chromatography, and de novo sequenced using mass spectrometry. In parallel, the Abs were isotyped using a human isotyping kit.

Figure 5:
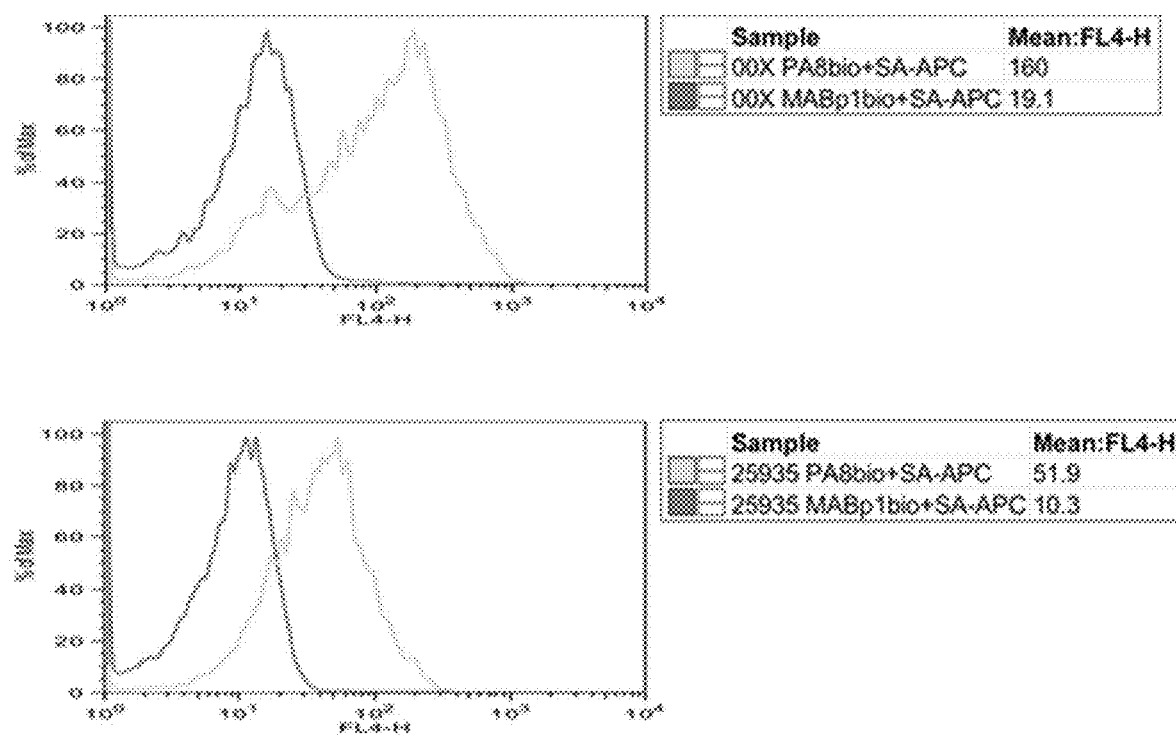
FIG. 5 is a set of two graphs showing the fluorescence intensity of clinical isolate 00X (top) or ATCC #25923 (bottom) pre-incubated with human sera for 15 minutes prior to the addition of biotinylated PA8-G3 Ab or negative control MABP1 Ab, and then incubated with streptavidin APC.

One of the isolated Abs was identified as being in the VH3 subfamily and having an IgG2 heavy chain and VK1 light chain. B-cells were isolated from the donor blood using a kit obtained from STEMCELL Technologies, Inc. Their RNA was extracted using a Trizol extraction protocol, and cDNA was generated using SuperScript III. Leader-specific primers were used to amplify the corresponding heavy and light chains of the Ab and a "directed" ScFv library was generated. The library was panned against wildtype SpA antigen for 7 rounds. The clones were screened using direct and sandwich ELISA with wildtype SpA. The selected clones were sequenced, and the heavy and light chains were cloned into vectors with an IgG3 constant (Fc) region (one that lacks the SpA recognition site in the Fab regions). The vectors were transfected into CHO cell lines, and high producing clones were picked. The purified Abs were tested for anti-SpA activity. The clones were scaled up for large-scale production, and the produced Abs were purified and used for further analyses. Examples of eight such Abs are described below:

PA8-G3 Ab

Heavy chain variable domain of SEQ ID NO: 5.

Heavy chain CDRs 1, 2, and 3 of SEQ ID NOs: 2, 3, and 4, respectively.

Heavy chain of SEQ ID NO: 6.

Light chain variable domain of SEQ ID NO: 10.

Light chain CDRs 1, 2, and 3 of SEQ ID NO: 7, 8, and 9, respectively.

Light chain of SEQ ID NO: 11.

PA4-G3 Ab

Heavy chain variable domain of SEQ ID NO: 15.

Heavy chain CDRs 1, 2, and 3 of SEQ ID NOs: 12, 13, and 14, respectively.

Heavy chain of SEQ ID NO: 16.

Light chain variable domain of SEQ ID NO: 20.

Light chain CDRs 1, 2, and 3 of SEQ ID NOs: 17, 18, and 19, respectively.

Light chain of SEQ ID NO: 21.

PA7.2-G3 Ab

Heavy chain variable domain of SEQ ID NO: 25.

Heavy chain CDRs 1, 2, and 3 of SEQ ID NOs: 22, 23, and 24, respectively.

Heavy chain of SEQ ID NO: 26.

Light chain variable domain of SEQ ID NO: 30.

Light chain CDRs 1, 2, and 3 of SEQ ID NOs: 27, 28, and 29, respectively.

Light chain of SEQ ID NO: 31,

PA15-G3 Ab

Heavy chain variable domain of SEQ ID NO: 35.

Heavy chain CDRs 1, 2, and 3 of SEQ ID NOs: 32, 33, and 34, respectively.

Heavy chain of SEQ ID NO: 36.

Light chain variable domain of SEQ ID NO: 40.

Light chain CDRs 1, 2, and 3 of SEQ ID NOs: 37, 38, and 39, respectively.

Light chain of SEQ ID NO: 41.

PA21-G3 Ab

Heavy chain variable domain of SEQ ID NO: 45.

Heavy chain CDRs 1, 2, and 3 of SEQ ID NOs: 42, 43, and 44, respectively.

Heavy chain of SEQ ID NO: 46.

Light chain variable domain of SEQ ID NO: 50.

Light chain CDRs 1, 2, and 3 of SEQ ID NOs: 47, 48, and 49, respectively.

Light chain of SEQ ID NO: 51.

PA27-G3 Ab

Heavy chain variable domain of SEQ ID NO: 55.

Heavy chain CDRs 1, 2, and 3 of SEQ ID NOs: 52, 53, and 54, respectively.

Heavy chain of SEQ ID NO: 56.

Light chain variable domain of SEQ ID NO: 60.

Light chain CDRs 1, 2, and 3 of SEQ ID NOs: 57, 58, and 59, respectively.

Light chain of SEQ ID NO: 61.

PA32-G3 Ab

Heavy chain variable domain of SEQ ID NO: 65.

Heavy chain CDRs 1, 2, and 3 of SEQ ID NOs: 62, 63, and 64, respectively.

Heavy chain of SEQ ID NO: 66.

Light chain variable domain of SEQ ID NO: 70.

Light chain CDRs 1, 2, and 3 of SEQ ID NO: 67, 68, and 69, respectively.

Light chain of SEQ ID NO: 71.

PA37-G3 Ab

Heavy chain variable domain of SEQ ID NO: 75.

Heavy chain CDRs 1, 2, and 3 of SEQ ID NOs: 72, 73, and 74, respectively.

Heavy chain of SEQ ID NO: 76.

Light chain variable domain of SEQ ID NO: 80.

Light chain CDRs 1, 2, and 3 of SEQ ID NOs: 77, 78, and 79, respectively.

Light chain of SEQ ID NO: 81.

A set of experiments was performed to determine whether the PA8-G3 Ab would be capable of binding to SpA on the cell wall of SA. In these experiments, SA stains ATCC #25923 or clinical isolate 00X were incubated either with (i) biotinylated PA8-G3, and then streptavidin-APC to fluorescently quantify the amount of biotin-PA-G3 bound on the SA surface (FIG. 2) or (ii) purified unlabeled PA8-G3 Ab, followed by biotinylated recombinant Fcγ receptor 1, and then streptavidin-APC to fluorescently quantify the amount of PA8-G3 bound to the SA surface that would lead to phagocytosis (i.e., have free Fc regions available to bind the recombinant Fcγ receptor 1) (FIG. 3). An anti-interleukin-1a Ab (MABp1) was used as a negative control in these experiments. The data in FIG. 2 show that PA8-G3 binds to SpA in the cell wall of SA and the data in FIG. 3 indicate that the bound PA8-G3 Ab had its Fc regions available to interact with FcR suggesting that the Ab would able to mediate opsinophagocytosis of SA in human subjects (as opposed to having its Fc regions bound to SpA and not able to engage FcRs and therefore mediate opsinophagocytosis of the bacteria).

A further set of experiments was performed to test whether binding of PA8-G3 Ab to the surface of SA would be recognized by the Fc γ receptors on phagocytes. In these experiments, two different strains of pH-rodo-green labeled *S. aureus* (clinical isolate 00X or ATCC #25923) were incubated with either unlabeled PA8-G3 Ab or a control Ab (MABp1), and then incubated with differentiated HL-60 cells. The resulting fluorescence of the HL-60 cells was determined using fluorescence-assisted cell sorting (FACS). The data show that PA8-G3 binds to the cell wall of both SA strains and mediates phagocytosis through the Fcγ receptors on the surface of HL-60 cells (FIG. 4). The successful phagocytosis by differentiated HL-60 cells of *S. aureus* bound to PA8-G3 was also evident from fluorescence microscopy experiments.

Surface plasmon resonance was used to determining the binding kinetics of PA8-G3 to SpA. In these experiments, PA8-G3 Ab was immobilized using anti-human capture sensor and commercial wildtype SpA. These data show that PA8-G3 has a $K_D$ of 5.38 pM. This affinity is approximately 1000-fold higher than the nanomolar affinity of human serum IgG1, IgG2, and IgG4 to SpA.

An additional set of experiments was performed to determine whether PA8-G3 Ab would be able to successfully compete for binding to SpA with human IgG bound to SpA through their Fc receptor. In these experiments, two different *S. aureus* strains were pre-incubated with human sera (which contains a high concentration of Igs which bind SpA via their Fc regions) for 15 minutes prior to incubation with biotinylated PA8-G3 Ab or biotinylated MABp1-IgG3 Ab (isotype-matched negative control), then treated with streptavidin APC, and then fluorescence was determined by flow cytometry. The data show that PA8-G3 Ab was able bind SpA having human IgG Abs bound to SpA by their Fc domain (FIG. 5).

In another set of experiments, PA8-G3 antibody was shown to compete with MABp1-IgG1 (which binds SpA via its Fc region) binding on SpA-coated beads. Pre-incubating the SpA beads with PA8-G3 reduced later added MABp1-IgG1 binding by 80.3%. Conversely, with SpA beads pre-incubated with MABp1-IgG1, later added PA8-G3 bound greater than >30% of the SpA beads surfaces within 15 minutes, whereas later added MABp1-IgG3 (isotype-matched negative control having the Fab of MABp1 and a human IgG3 Fc) did not significantly bind to SpA beads pre-incubated with MABp1-IgG1.

Figure 6:
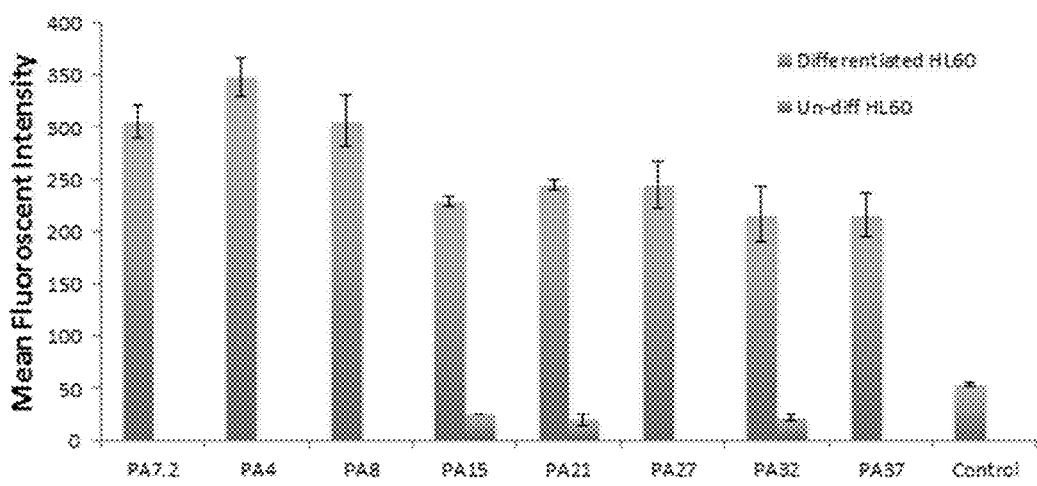
FIG. 6 is a graph showing the mean fluorescent intensity of differentiated or undifferentiated HL-60 cells after co-incubation with pH-rodo-green labeled SA and one of the following unlabeled Abs: PA7.2-G3, PA4-G3, PA8-G3, PA15-G3, PA21-G3, PA27-G3, PA32-G3, PA37-G3, or MABp1. The MABp1 Ab samples were used as a negative control.
Figure 7A:
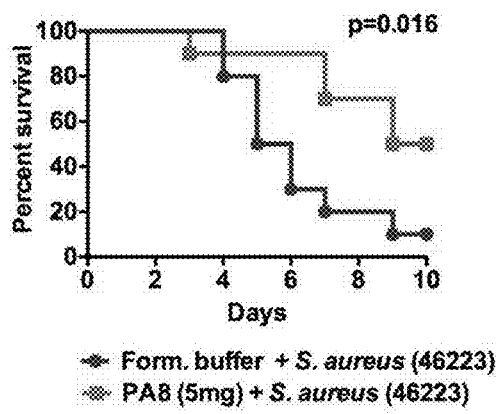
FIGS. 7A-D are graphs showing that administration of mAb PA8 enhances the survival of murine subjects infected with S. aureus.
Figure 7B:
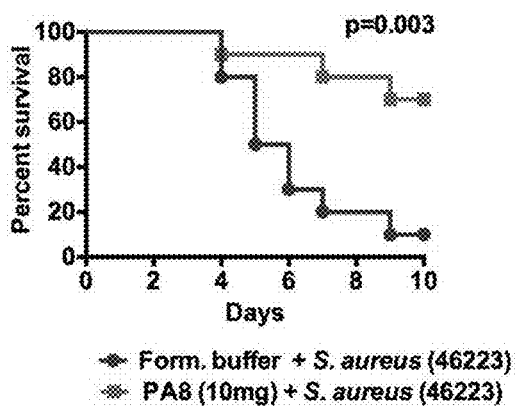
Figure 7C:
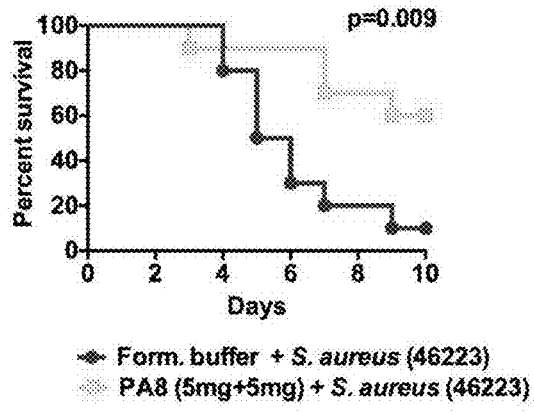
Figure 7D:
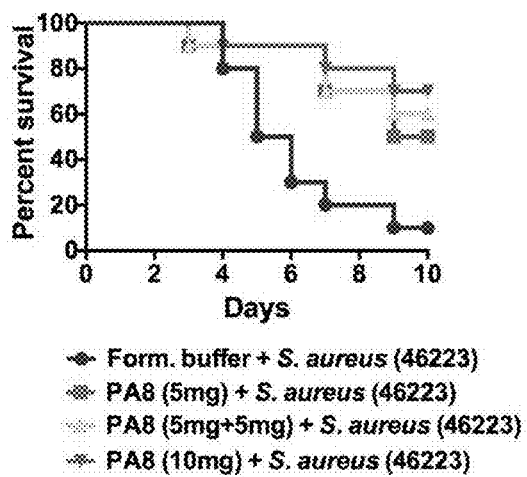

An additional set of experiments was performed to test the ability of additional anti-SpA Abs to promote phagocytosis of SA by differentiated HL-60 cells. In these experiments, differentiated HL-60 cells were co-incubated with pH-rodo-green labeled *S. aureus* and one of the following Abs: PA7.2-G3, PA4-G3, PA8-G3, PA15-G3, PA21-G3, PA27-G3, PA32-G3, PA37-G3, or MABp1. MABp1 was used as a negative control in these experiments. The data show that all of the tested anti-SpA Abs were able to promote opsinization and phagocytosis of *S. aureus* by differentiated HL-60 cells (FIG. 6).

Additional Bio-Layer Interferometry (using done using a ForteBio Octet Red 96 instrument) experiments were performed to determine the $K_D$ of seven additional anti-SpA Abs (performed using 20 nM antigen). The resulting data showed that PA7.2-G3 has a $K_D$ of less than $1 \times 10^{-12}$ M, PA4-G3 has a $K_D$ of $5.38 \times 10^{-12}$ M, PA15-G3 has a $K_D$ of less than $1 \times 10^{-12}$ M, PA21-G3 has a $K_D$ of less than $1 \times 10^{-12}$ M, PA27-G3 has a $K_D$ of less than $1 \times 10^{-12}$ M, PA32-G3 has a $K_D$ of less than $1 \times 10^{-12}$ M, and PA37-G3 has a $K_D$ of less than $1 \times 10^{-12}$ M.

In sum, the data show that the Abs provided herein can bind with very high affinity to SpA in the cell wall of SA, promote phagocytosis by immune cells, and are capable of doing so in the presence of human IgGs bound to SpA by their Fc domain.

Example 2

In Vivo Survival Study of Monoclonal Antibody PA8 in Mice Bacteremia/Sepsis Model. Survival of mice from *S. aureus* bacteremica was examined using prophylactic doses of PA8 (the monoclonal antibody termed PA8-G3 described in Example 1).

Female Balb/C mice (6-8 weeks of age) were purchased from Charles River Laboratory, NIH, Maryland. Upon arrival, the mice were examined, group housed (10/cage) in cages with absorbent bedding. All mice were placed under the required husbandry standards found in the NIH Guide for the Care and Use of Laboratory Animals.

The protective efficacy of PA8 was investigated in the SA sepsis model induced by intravenous injections (i.v.) of $2 \times 10^7$ CFUs of MRSA strain NR-46223. Mice were treated intravenously with PA8 at specific doses (5 mg or 10 mg) 3 h prior to MRSA infection or two doses of 5 mg each at day 0 and 3. Control mice were treated with formulation buffer only. The mice were followed for 10 days (twice per day) at which point all remaining mice were sacrificed.

Three hours after the PA8/formulation buffer (0.1 ml) i.v. administration, the mice were challenged with a single intravenous (IV) injection of *S. aureus* strain NR-46223 ($2 \times 10^7$ CFU in 0.1 ml). One set of mice was given two doses of 5 mg each at day 0 and 3. Significant differences in the relative survival times between treatment groups were detected. Referring to FIG. 7A-D, passive administration of single dose of 5 mg (A) or 10 mg (B), or two doses of 5 mg at day 0 & day 3 (C), of mAb PA8 (intravenously) enhances the survival of BALB/c mice significantly higher than formulation buffer treatment in dose dependent manner (10 mice per group) with *Staphylococcus aureus* sepsis (induced by intravenous injection of $2 \times 10^7$ colony-forming units of methicillin-resistant *S. aureus* strain NR-46223). Section (D) shows the survival using all different treatment in one graph. Fifty percent (5/10) of the mice survived that received 5 mg of Mab PA8 (p=0.016), sixty percent that received two doses of 5 mg each (p=0.09), and seventy percent (7/10) that received 10 mg of mAb PA8 (p=0.003) compared to 10% (1/10) of mice that received formulation buffer (1/10) survived the bacterial challenge with *S. aureus* NR-46223. Statistical analysis of the animal data was conducted using Kaplan-Meier Survival Analysis with a Mantel-Cox (logrank) test. These results clearly indicate that PA8 provides a significant level of protection against lethal infection with *S. aureus* MRSA strain.

Example 3

Figure 8A:
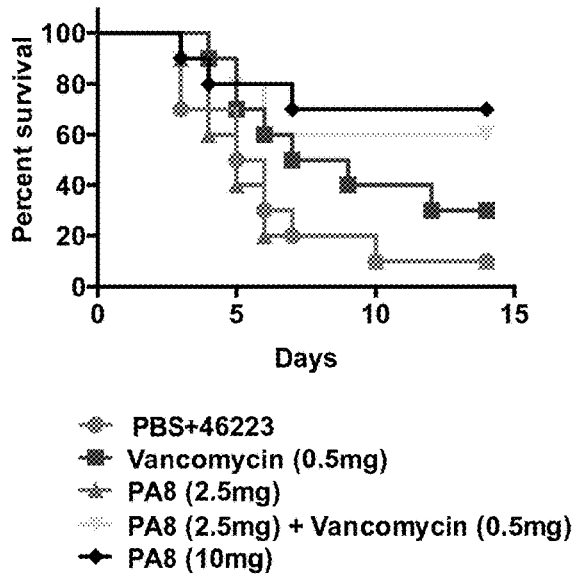
FIGS. 8A-C are graphs showing the synergy between PA8-G3 and vancomycin.
Figure 8B:
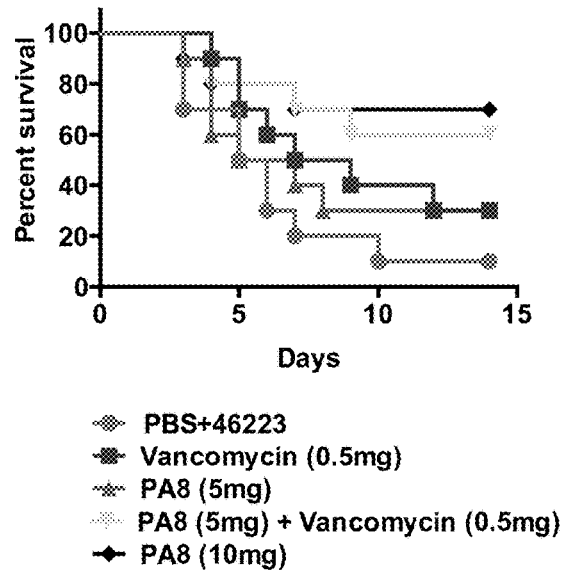
Figure 8C:
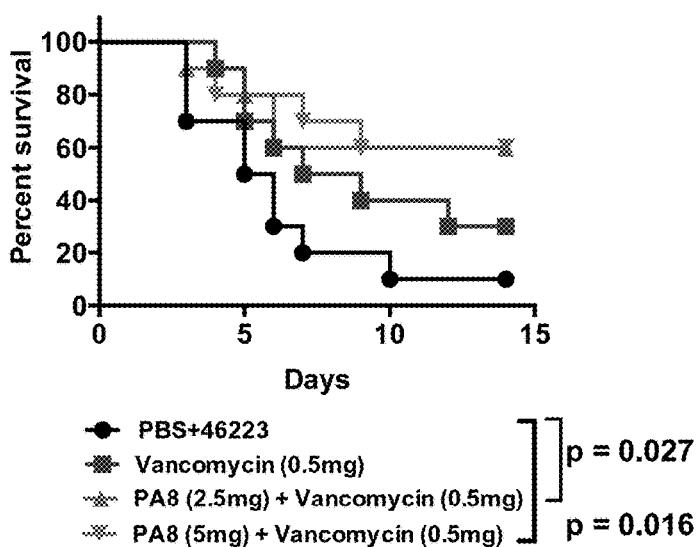

Female Balb/C mice (10 per group) from Charles River Laboratory were injected with 0.5 mg of vancomycin via intraperitoneal route, along with different sub-optimal doses of PA8-G3 (0 mg, 2.5 mg and 5 mg via intravenous route) two hours prior to infection with MRSA (NR 46223 at $3 \times 10^7$ CFU i.v.). The mice were observed for 14 days. Referring to FIGS. 8A-C, at day 14, only 10% of the PBS treated mice survived, 30% of the vancomycin treated mice survived. However, when 2.5 mg of PA8-G3 was injected along with vancomycin treatment, then 60% of the animals survived (p=0.027), and when 5 mg of PA8-G3 was injected with vancomycin, then 60% of the animals survived and those mice that died lived longer than the lower dosage (p=0.016). This data indicates that sub-efficacious doses of PA8-G3 can rescue animals from SA mediated bacteremia, when co-treated with sub-optimal dose of vancomycin. Statistical analysis of the animal data was conducted using Kaplan-Meier Survival Analysis with a Mantel-Cox (logrank) test.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition comprising a pharmaceutically acceptable carrier and a purified monoclonal antibody which specifically binds *Staphylococcus aureus* protein A (SpA) with a KD of less than $1 \times 10^{-10}$ M via its Fab region paratope and has an Fc region able to interact with an FcR when the antibody is bound to SpA by its Fab region paratope and wherein the antibody comprises a human IgG$_3$ constant region that lacks a SpA recognition site in its Fab regions or a humanized IgG$_3$ constant region that tacks a SpA recognition site in its Fab regions, and wherein said antibody is able to displace human IgG immunoglobulins bound to SpA on *Staphylococcus aureus* bacteria via their Fc regions.

2. The pharmaceutical composition of claim 1, wherein the Fab region paratope of the antibody binds an epitope within the IgG-binding and Xr repeat sequences of SpA.

* * * * *

SEQUENCE LISTING

<160> NUMBER OF SEQ ID NOS: 86

<210> SEQ ID NO 1
<211> LENGTH: 20
<212> TYPE: PRT
<213> ORGANISM: Staphylococcus aureus
<220> FEATURE:
<223> OTHER INFORMATION: Antigenic Peptide #5

<400> SEQUENCE: 1

Lys Pro Gly Lys Glu Asp Asn Lys Lys Pro Gly Lys Glu Asp Gly Asn
1               5                   10                  15

Lys Pro Gly Lys
            20

<210> SEQ ID NO 2
<211> LENGTH: 5
<212> TYPE: PRT
<213> ORGANISM: Homo sapiens
<220> FEATURE:
<223> OTHER INFORMATION: PA8-G3 Heavy Chain CDR1

<400> SEQUENCE: 2

Thr Tyr Gly Met Ser
1               5

<210> SEQ ID NO 3
<211> LENGTH: 17
<212> TYPE: PRT
<213> ORGANISM: Homo sapiens
<220> FEATURE:
<223> OTHER INFORMATION: PA8-G3 Heavy Chain CDR2

<400> SEQUENCE: 3

Ser Ile Thr Gly Ser Gly Arg Ser Thr Phe Tyr Ala Asp Ser Val Lys
1               5                   10                  15

Gly

<210> SEQ ID NO 4
<211> LENGTH: 16
<212> TYPE: PRT
<213> ORGANISM: Homo sapiens
<220> FEATURE:
<223> OTHER INFORMATION: PA8-G3 Heavy Chain CDR3

<400> SEQUENCE: 4

Ser Pro Ala Asp Ile Val Thr Gly Tyr Tyr Pro Trp Trp Phe Asp Leu
1               5                   10                  15

<210> SEQ ID NO 5
<211> LENGTH: 125
<212> TYPE: PRT
<213> ORGANISM: Homo sapiens
<220> FEATURE:
<223> OTHER INFORMATION: PA8-G3 Heavy Chain Variable Domain

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ser Ser Ile Thr Gly Ser Gly Arg Ser Thr Phe Tyr Ala Asp Ser Val

```
                    50                  55                  60
Lys Gly Arg Phe Thr Ile Ser Arg Asp Asn Ser Thr Asn Thr Leu Ser
 65                  70                  75                  80

Leu Gln Met Asn Ser Leu Arg Ala Glu Asp Thr Ala Val Tyr Tyr Cys
                     85                  90                  95

Ala Arg Ser Pro Ala Asp Ile Val Thr Gly Tyr Tyr Pro Trp Trp Phe
                100                 105                 110

Asp Leu Trp Gly Gln Gly Thr Leu Val Thr Val Ser Ser
                115                 120                 125

<210> SEQ ID NO 6
<211> LENGTH: 502
<212> TYPE: PRT
<213> ORGANISM: Homo sapiens
<220> FEATURE:
<223> OTHER INFORMATION: PA8-G3 Heavy Chain

<400> SEQUENCE: 6

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
                 20                  25                  30

Gly Met Ser Trp Val Arg Gln Ala Pro Gly Lys Gly Leu Glu Trp Val
             35                  40                  45

Ser Ser Ile Thr Gly Ser Gly Arg Ser Thr Phe Tyr Ala Asp Ser Val
         50                  55                  60

Lys Gly Arg Phe Thr Ile Ser Arg Asp Asn Ser Thr Asn Thr Leu Ser
 65                  70                  75                  80

Leu Gln Met Asn Ser Leu Arg Ala Glu Asp Thr Ala Val Tyr Tyr Cys
                     85                  90                  95

Ala Arg Ser Pro Ala Asp Ile Val Thr Gly Tyr Tyr Pro Trp Trp Phe
                100                 105                 110

Asp Leu Trp Gly Gln Gly Thr Leu Val Thr Val Ser Ser Ala Ser Thr
                115                 120                 125

Lys Gly Pro Ser Val Phe Pro Leu Ala Pro Cys Ser Arg Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Thr Cys
                195                 200                 205

Asn Val Asn His Lys Pro Ser Asn Thr Lys Val Asp Lys Arg Val Glu
            210                 215                 220

Leu Lys Thr Pro Leu Gly Asp Thr Thr His Thr Cys Pro Arg Cys Pro
225                 230                 235                 240

Glu Pro Lys Ser Cys Asp Thr Pro Pro Cys Pro Arg Cys Pro Glu
                245                 250                 255

Pro Lys Ser Cys Asp Thr Pro Pro Cys Pro Arg Cys Pro Glu Pro
                260                 265                 270

Lys Ser Cys Asp Thr Pro Pro Cys Pro Arg Cys Pro Ala Pro Glu
            275                 280                 285

Leu Leu Gly Gly Pro Ser Val Phe Leu Phe Pro Pro Lys Pro Lys Asp
```

```
                290                 295                 300
Thr Leu Met Ile Ser Arg Thr Pro Glu Val Thr Cys Val Val Val Asp
305                 310                 315                 320

Val Ser His Glu Asp Pro Glu Val Gln Phe Lys Trp Tyr Val Asp Gly
                325                 330                 335

Val Glu Val His Asn Ala Lys Thr Lys Pro Arg Glu Glu Gln Tyr Asn
            340                 345                 350

Ser Thr Phe Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Thr Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Ser Gly Gln Pro Glu Asn Asn Tyr Asn Thr
        435                 440                 445

Thr Pro Pro Met Leu Asp Ser Asp Gly Ser Phe Phe Leu Tyr Ser Lys
    450                 455                 460

Leu Thr Val Asp Lys Ser Arg Trp Gln Gln Gly Asn Ile Phe Ser Cys
465                 470                 475                 480

Ser Val Met His Glu Ala Leu His Asn Arg Phe Thr Gln Lys Ser Leu
                485                 490                 495

Ser Leu Ser Pro Gly Lys
            500

<210> SEQ ID NO 7
<211> LENGTH: 11
<212> TYPE: PRT
<213> ORGANISM: Homo sapiens
<220> FEATURE:
<223> OTHER INFORMATION: PA8-G3 Light Chain CDR1

<400> SEQUENCE: 7

Arg Ala Ser Gln Ser Ile Asn Thr Tyr Leu Asn
1               5                   10

<210> SEQ ID NO 8
<211> LENGTH: 7
<212> TYPE: PRT
<213> ORGANISM: Homo sapiens
<220> FEATURE:
<223> OTHER INFORMATION: PA8-G3 Light Chain CDR2

<400> SEQUENCE: 8

Gly Ala Ser Ser Leu Gln Ser
1               5

<210> SEQ ID NO 9
<211> LENGTH: 9
<212> TYPE: PRT
<213> ORGANISM: Homo sapiens
<220> FEATURE:
<223> OTHER INFORMATION: PA8-G3 Light Chain CDR3

<400> SEQUENCE: 9

Gln Gln Ala Asn Ser Phe Pro Leu Thr
1               5
```

```
<210> SEQ ID NO 10
<211> LENGTH: 108
<212> TYPE: PRT
<213> ORGANISM: Homo sapiens
<220> FEATURE:
<223> OTHER INFORMATION: PA8-G3 Light Chain Variable Domain

<400> SEQUENCE: 10

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Ser Ile Asn Thr Tyr
            20                  25                  30

Leu Asn Trp Tyr Gln Gln Lys Pro Gly Lys Ala Pro Arg Leu Leu Ile
        35                  40                  45

Ala Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gln Gly Thr Arg Leu Glu Ile Lys Arg
            100                 105

<210> SEQ ID NO 11
<211> LENGTH: 214
<212> TYPE: PRT
<213> ORGANISM: Homo sapiens
<220> FEATURE:
<223> OTHER INFORMATION: PA8-G3 Light Chain

<400> SEQUENCE: 11

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Ser Ile Asn Thr Tyr
            20                  25                  30

Leu Asn Trp Tyr Gln Gln Lys Pro Gly Lys Ala Pro Arg Leu Leu Ile
        35                  40                  45

Ala Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Glu Cys
                210

<210> SEQ ID NO 12
<211> LENGTH: 5
<212> TYPE: PRT
<213> ORGANISM: Homo sapiens
<220> FEATURE:
<223> OTHER INFORMATION: PA4-G3 Heavy Chain CDR1

<400> SEQUENCE: 12

Ser Tyr Ala Met Ser
1               5

<210> SEQ ID NO 13
<211> LENGTH: 17
<212> TYPE: PRT
<213> ORGANISM: Homo sapiens
<220> FEATURE:
<223> OTHER INFORMATION: PA4-G3 Heavy Chain CDR2

<400> SEQUENCE: 13

Ala Ile Thr Gly Ser Gly Gly Ser Thr Tyr Tyr Ala Asp Ser Val Lys
1               5                   10                  15

Gly

<210> SEQ ID NO 14
<211> LENGTH: 8
<212> TYPE: PRT
<213> ORGANISM: Homo sapiens
<220> FEATURE:
<223> OTHER INFORMATION: PA4-G3 Heavy Chain CDR3

<400> SEQUENCE: 14

Gly Asp Ile Thr Ser Gly Phe Gly
1               5

<210> SEQ ID NO 15
<211> LENGTH: 117
<212> TYPE: PRT
<213> ORGANISM: Homo sapiens
<220> FEATURE:
<223> OTHER INFORMATION: PA4-G3 Heavy Chain Variable Domain

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Thr Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Ile Thr Ser Gly Phe Gly Trp Gly Gln Gly Thr Leu
            100                 105                 110

Val Thr Val Ser Ser
            115

<210> SEQ ID NO 16
<211> LENGTH: 494
<212> TYPE: PRT
<213> ORGANISM: Homo sapiens
<220> FEATURE:
<223> OTHER INFORMATION: PA4-G3 Heavy Chain

<400> SEQUENCE: 16

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Ile Thr Ser Gly Phe Gly Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Thr Cys Asn Val Asn His Lys Pro Ser Asn
        195                 200                 205

Thr Lys Val Asp Lys Arg Val Glu Leu Lys Thr Pro Leu Gly Asp Thr
    210                 215                 220

Thr His Thr Cys Pro Arg Cys Pro Glu Pro Lys Ser Cys Asp Thr Pro
225                 230                 235                 240

Pro Pro Cys Pro Arg Cys Pro Glu Pro Lys Ser Cys Asp Thr Pro Pro
                245                 250                 255

Pro Cys Pro Arg Cys Pro Glu Pro Lys Ser Cys Asp Thr Pro Pro Pro
            260                 265                 270

Cys Pro Arg Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Gln Phe Lys Trp Tyr Val Asp Gly Val Glu Val His Asn Ala Lys Thr
                325                 330                 335

Lys Pro Arg Glu Glu Gln Tyr Asn Ser Thr Phe Arg Val Val Ser Val
            340                 345                 350

Leu Thr Val Leu His Gln Asp Trp Leu Asn Gly Lys Glu Tyr Lys Cys
        355                 360                 365

```
Lys Val Ser Asn Lys Ala Leu Pro Ala Pro Ile Glu Lys Thr Ile Ser
            370                 375                 380

Lys Thr Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Ser Gly
            420                 425                 430

Gln Pro Glu Asn Asn Tyr Asn Thr Thr Pro Pro Met Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Ile Phe Ser Cys Ser Val Met His Glu Ala Leu His
465                 470                 475                 480

Asn Arg Phe Thr Gln Lys Ser Leu Ser Leu Ser Pro Gly Lys
                485                 490

<210> SEQ ID NO 17
<211> LENGTH: 11
<212> TYPE: PRT
<213> ORGANISM: Homo sapiens
<220> FEATURE:
<223> OTHER INFORMATION: PA4-G3 Light Chain CDR1

<400> SEQUENCE: 17

Arg Ala Ser Gln Gly Ile Arg Asn Asp Leu Gly
1               5                   10

<210> SEQ ID NO 18
<211> LENGTH: 7
<212> TYPE: PRT
<213> ORGANISM: Homo sapiens
<220> FEATURE:
<223> OTHER INFORMATION: PA4-G3 Light Chain CDR2

<400> SEQUENCE: 18

Ala Ala Ser Ser Leu Gln Ser
1               5

<210> SEQ ID NO 19
<211> LENGTH: 9
<212> TYPE: PRT
<213> ORGANISM: Homo sapiens
<220> FEATURE:
<223> OTHER INFORMATION: PA4-G3 Light Chain CDR3

<400> SEQUENCE: 19

Gln Gln Ser Tyr Ser Thr Pro Trp Thr
1               5

<210> SEQ ID NO 20
<211> LENGTH: 108
<212> TYPE: PRT
<213> ORGANISM: Homo sapiens
<220> FEATURE:
<223> OTHER INFORMATION: PA4-G3 Light Chain Variable Domain

<400> SEQUENCE: 20

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

```
Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg
                100                 105

<210> SEQ ID NO 21
<211> LENGTH: 214
<212> TYPE: PRT
<213> ORGANISM: Homo sapiens
<220> FEATURE:
<223> OTHER INFORMATION: PA4-G3 Light Chain

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 22
<211> LENGTH: 5
<212> TYPE: PRT
<213> ORGANISM: Homo sapiens
<220> FEATURE:
<223> OTHER INFORMATION: PA7.2-G3 Heavy Chain CDR1

<400> SEQUENCE: 22

Asn Tyr Ala Met Ser
```

-continued

<210> SEQ ID NO 23
<211> LENGTH: 17
<212> TYPE: PRT
<213> ORGANISM: Homo sapiens
<220> FEATURE:
<223> OTHER INFORMATION: PA7.2-G3 Heavy Chain CDR2

<400> SEQUENCE: 23

Thr Ile Ser Gly Ser Asp Gly Gly Thr Tyr Tyr Ala Asp Ser Val Lys
1               5                   10                  15
Gly

<210> SEQ ID NO 24
<211> LENGTH: 12
<212> TYPE: PRT
<213> ORGANISM: Homo sapiens
<220> FEATURE:
<223> OTHER INFORMATION: PA7.2-G3 Heavy Chain CDR3

<400> SEQUENCE: 24

Val Gly Leu Ser Ala Pro Val Thr Phe Phe Asp Phe
1               5                   10

<210> SEQ ID NO 25
<211> LENGTH: 121
<212> TYPE: PRT
<213> ORGANISM: Homo sapiens
<220> FEATURE:
<223> OTHER INFORMATION: PA7.2-G3 Heavy Chain Variable Domain

<400> SEQUENCE: 25

Glu Val Gln Leu Val Glu Ser Arg Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Asp Gly Gly Thr Tyr Tyr Ala Asp Ser Val
    50                  55                  60

Lys Gly Arg Phe Thr Ile Ser Arg Asp Asn Ser Gly Asn Thr Val Tyr
65                  70                  75                  80

Leu Gln Met Asn Ser Leu Arg Glu Asp Thr Ala Val Tyr Tyr Cys
                85                  90                  95

Ala Arg Val Gly Leu Ser Ala Pro Val Thr Phe Phe Asp Phe Trp Gly
            100                 105                 110

Gln Gly Thr Leu Val Thr Val Ser Ser
        115                 120

<210> SEQ ID NO 26
<211> LENGTH: 498
<212> TYPE: PRT
<213> ORGANISM: Homo sapiens
<220> FEATURE:
<223> OTHER INFORMATION: PA7.2-G3 Heavy Chain

<400> SEQUENCE: 26

Glu Val Gln Leu Val Glu Ser Arg Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

```
Ala Met Ser Trp Val Arg Gln Ala Pro Gly Lys Gly Leu Glu Trp Val
         35                  40                  45

Ser Thr Ile Ser Gly Ser Asp Gly Thr Tyr Tyr Ala Asp Ser Val
 50                  55                  60

Lys Gly Arg Phe Thr Ile Ser Arg Asp Asn Ser Gly Asn Thr Val Tyr
 65                  70                  75                  80

Leu Gln Met Asn Ser Leu Arg Glu Asp Asp Thr Ala Val Tyr Tyr Cys
                 85                  90                  95

Ala Arg Val Gly Leu Ser Ala Pro Val Thr Phe Phe Asp Phe Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asn His
            195                 200                 205

Lys Pro Ser Asn Thr Lys Val Asp Lys Arg Val Glu Leu Lys Thr Pro
210                 215                 220

Leu Gly Asp Thr Thr His Thr Cys Pro Arg Cys Pro Glu Pro Lys Ser
225                 230                 235                 240

Cys Asp Thr Pro Pro Pro Cys Pro Arg Cys Pro Glu Pro Lys Ser Cys
                245                 250                 255

Asp Thr Pro Pro Pro Cys Pro Arg Cys Pro Glu Pro Lys Ser Cys Asp
            260                 265                 270

Thr Pro Pro Pro Cys Pro Arg Cys Pro Ala Pro Glu Leu Leu Gly Gly
            275                 280                 285

Pro Ser Val Phe Leu Phe Pro Lys Pro Lys Asp Thr Leu Met Ile
290                 295                 300

Ser Arg Thr Pro Glu Val Thr Cys Val Val Val Asp Val Ser His Glu
305                 310                 315                 320

Asp Pro Glu Val Gln Phe Lys Trp Tyr Val Asp Gly Val Glu Val His
                325                 330                 335

Asn Ala Lys Thr Lys Pro Arg Glu Glu Gln Tyr Asn Ser Thr Phe Arg
            340                 345                 350

Val Val Ser Val Leu Thr Val Leu His Gln Asp Trp Leu Asn Gly Lys
            355                 360                 365

Glu Tyr Lys Cys Lys Val Ser Asn Lys Ala Leu Pro Ala Pro Ile Glu
370                 375                 380

Lys Thr Ile Ser Lys Thr Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Ser Gly Gln Pro Glu Asn Asn Tyr Asn Thr Thr Pro Pro Met
            435                 440                 445
```

```
Leu Asp Ser Asp Gly Ser Phe Phe Leu Tyr Ser Lys Leu Thr Val Asp
            450                 455                 460

Lys Ser Arg Trp Gln Gln Gly Asn Ile Phe Ser Cys Ser Val Met His
465                 470                 475                 480

Glu Ala Leu His Asn Arg Phe Thr Gln Lys Ser Leu Ser Leu Ser Pro
                    485                 490                 495

Gly Lys

<210> SEQ ID NO 27
<211> LENGTH: 11
<212> TYPE: PRT
<213> ORGANISM: Homo sapiens
<220> FEATURE:
<223> OTHER INFORMATION: PA7.2-G3 Light Chain CDR1

<400> SEQUENCE: 27

Arg Ala Ser Gln Ser Ile Ser Ser Tyr Leu Asn
1               5                   10

<210> SEQ ID NO 28
<211> LENGTH: 7
<212> TYPE: PRT
<213> ORGANISM: Homo sapiens
<220> FEATURE:
<223> OTHER INFORMATION: PA7.2-G3 Light Chain CDR2

<400> SEQUENCE: 28

Ala Ala Ser Ser Leu Gln Ser
1               5

<210> SEQ ID NO 29
<211> LENGTH: 9
<212> TYPE: PRT
<213> ORGANISM: Homo sapiens
<220> FEATURE:
<223> OTHER INFORMATION: PA7.2-G3 Light Chain CDR3

<400> SEQUENCE: 29

Gln Gln Ser Tyr Arg Thr Pro Phe Ser
1               5

<210> SEQ ID NO 30
<211> LENGTH: 108
<212> TYPE: PRT
<213> ORGANISM: Homo sapiens
<220> FEATURE:
<223> OTHER INFORMATION: PA7.2-G3 Light Chain Variable Domain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Thr Pro Phe
                85                  90                  95

Ser Phe Gly Gln Gly Thr Asp Leu Asp Leu Lys Arg
```

<210> SEQ ID NO 31
<211> LENGTH: 214
<212> TYPE: PRT
<213> ORGANISM: Homo sapiens
<220> FEATURE:
<223> OTHER INFORMATION: PA7.2-G3 Light Chain

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Thr Pro Phe
                85                  90                  95

Ser Phe Gly Gln Gly Thr Asp Leu Asp Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 5
<212> TYPE: PRT
<213> ORGANISM: Homo sapiens
<220> FEATURE:
<223> OTHER INFORMATION: PA15-G3 Heavy Chain CDR1

<400> SEQUENCE: 32

Thr Phe Ala Met Asn
1               5

<210> SEQ ID NO 33
<211> LENGTH: 17
<212> TYPE: PRT
<213> ORGANISM: Homo sapiens
<220> FEATURE:
<223> OTHER INFORMATION: PA15-G3 Heavy Chain CDR2

<400> SEQUENCE: 33

Ser Ile Ser Gly Ser Gly Gly Ser Thr Tyr Tyr Ala Asp Ser Val Lys
1               5                   10                  15

Gly

<210> SEQ ID NO 34
<211> LENGTH: 11
<212> TYPE: PRT
<213> ORGANISM: Homo sapiens
<220> FEATURE:
<223> OTHER INFORMATION: PA15-G3 Heavy Chain CDR3

<400> SEQUENCE: 34

Asp Phe Asn Trp Asp Ser Gly Thr Met Asp Leu
1               5                   10

<210> SEQ ID NO 35
<211> LENGTH: 120
<212> TYPE: PRT
<213> ORGANISM: Homo sapiens
<220> FEATURE:
<223> OTHER INFORMATION: PA15-G3 Heavy Chain Variable Domain

<400> SEQUENCE: 35

Glu Val Gln Leu Val Glu Thr Gly Gly Gly Leu Val Arg Pro Gly Gly
1               5                   10                  15

Ser Leu Arg Leu Ser Cys Ala Ala Ser Gly Leu Thr Phe Ser Thr Phe
            20                  25                  30

Ala Met Asn Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Phe Asn Trp Asp Ser Gly Thr Met Asp Leu Trp Gly Gln
            100                 105                 110

Gly Thr Thr Val Thr Val Ser Pro
        115                 120

<210> SEQ ID NO 36
<211> LENGTH: 497
<212> TYPE: PRT
<213> ORGANISM: Homo sapiens
<220> FEATURE:
<223> OTHER INFORMATION: PA15-G3 Heavy Chain

<400> SEQUENCE: 36

Glu Val Gln Leu Val Glu Thr Gly Gly Gly Leu Val Arg Pro Gly Gly
1               5                   10                  15

Ser Leu Arg Leu Ser Cys Ala Ala Ser Gly Leu Thr Phe Ser Thr Phe
            20                  25                  30

Ala Met Asn Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Phe Asn Trp Asp Ser Gly Thr Met Asp Leu Trp Gly Gln

```
            100                 105                 110
Gly Thr Thr Val Thr Val Ser Pro Ala Ser Thr Lys Gly Pro Ser Val
            115                 120                 125

Phe Pro Leu Ala Pro Cys Ser Arg Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Thr Cys Asn Val Asn His Lys
            195                 200                 205

Pro Ser Asn Thr Lys Val Asp Lys Arg Val Glu Leu Lys Thr Pro Leu
        210                 215                 220

Gly Asp Thr Thr His Thr Cys Pro Arg Cys Pro Glu Pro Lys Ser Cys
225                 230                 235                 240

Asp Thr Pro Pro Pro Cys Pro Arg Cys Pro Glu Pro Lys Ser Cys Asp
                245                 250                 255

Thr Pro Pro Pro Cys Pro Arg Cys Pro Glu Pro Lys Ser Cys Asp Thr
            260                 265                 270

Pro Pro Pro Cys Pro Arg Cys Pro Ala Pro Glu Leu Leu Gly Gly Pro
            275                 280                 285

Ser Val Phe Leu Phe Pro Pro Lys Pro Lys Asp Thr Leu Met Ile Ser
        290                 295                 300

Arg Thr Pro Glu Val Thr Cys Val Val Val Asp Val Ser His Glu Asp
305                 310                 315                 320

Pro Glu Val Gln Phe Lys Trp Tyr Val Asp Gly Val Glu Val His Asn
                325                 330                 335

Ala Lys Thr Lys Pro Arg Glu Glu Gln Tyr Asn Ser Thr Phe Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
        370                 375                 380

Thr Ile Ser Lys Thr Lys Gly Gln Pro Arg Glu Pro Gln Val Tyr Thr
385                 390                 395                 400

Leu Pro Pro Ser Arg Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Ser Gly Gln Pro Glu Asn Asn Tyr Asn Thr Thr Pro Pro Met Leu
            435                 440                 445

Asp Ser Asp Gly Ser Phe Phe Leu Tyr Ser Lys Leu Thr Val Asp Lys
        450                 455                 460

Ser Arg Trp Gln Gln Gly Asn Ile Phe Ser Cys Ser Val Met His Glu
465                 470                 475                 480

Ala Leu His Asn Arg Phe Thr Gln Lys Ser Leu Ser Leu Ser Pro Gly
                485                 490                 495

Lys

<210> SEQ ID NO 37
<211> LENGTH: 11
```

```
<212> TYPE: PRT
<213> ORGANISM: Homo sapiens
<220> FEATURE:
<223> OTHER INFORMATION: PA15-G3 Light Chain CDR1

<400> SEQUENCE: 37

Arg Ala Ser Gln Ser Ile Ser Ser Tyr Leu Asn
1               5                   10

<210> SEQ ID NO 38
<211> LENGTH: 7
<212> TYPE: PRT
<213> ORGANISM: Homo sapiens
<220> FEATURE:
<223> OTHER INFORMATION: PA15-G3 Light Chain CDR2

<400> SEQUENCE: 38

Ala Ala Ser Ser Leu Gln Ser
1               5

<210> SEQ ID NO 39
<211> LENGTH: 9
<212> TYPE: PRT
<213> ORGANISM: Homo sapiens
<220> FEATURE:
<223> OTHER INFORMATION: PA15-G3 Light Chain CDR3

<400> SEQUENCE: 39

Gln Gln Ser Tyr Ser Thr Pro Tyr Thr
1               5

<210> SEQ ID NO 40
<211> LENGTH: 108
<212> TYPE: PRT
<213> ORGANISM: Homo sapiens
<220> FEATURE:
<223> OTHER INFORMATION: PA15-G3 Light Chain Variable Domain

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg
            100                 105

<210> SEQ ID NO 41
<211> LENGTH: 214
<212> TYPE: PRT
<213> ORGANISM: Homo sapiens
<220> FEATURE:
<223> OTHER INFORMATION: PA15-G3 Light Chain

<400> SEQUENCE: 41

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
         195                 200                 205

Phe Asn Arg Gly Glu Cys
    210

<210> SEQ ID NO 42
<211> LENGTH: 5
<212> TYPE: PRT
<213> ORGANISM: Homo sapiens
<220> FEATURE:
<223> OTHER INFORMATION: PA21-G3 Heavy Chain CDR1

<400> SEQUENCE: 42

Ser Tyr Gly Met His
1               5

<210> SEQ ID NO 43
<211> LENGTH: 17
<212> TYPE: PRT
<213> ORGANISM: Homo sapiens
<220> FEATURE:
<223> OTHER INFORMATION: PA21-G3 Heavy Chain CDR2

<400> SEQUENCE: 43

Gly Ile Ser Gly Asp Ala Gly Ser Thr Tyr Tyr Ala Asp Ser Val Lys
1               5                   10                  15

Gly

<210> SEQ ID NO 44
<211> LENGTH: 13
<212> TYPE: PRT
<213> ORGANISM: Homo sapiens
<220> FEATURE:
<223> OTHER INFORMATION: PA21-G3 Heavy Chain CDR3

<400> SEQUENCE: 44

Val Met Asn Tyr Tyr Gly Pro Gly Ser Ala Phe Asp Tyr

<210> SEQ ID NO 45
<211> LENGTH: 122
<212> TYPE: PRT
<213> ORGANISM: Homo sapiens
<220> FEATURE:
<223> OTHER INFORMATION: PA21-G3 Heavy Chain Variable Domain

<400> SEQUENCE: 45

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ser Gly Ile Ser Gly Asp Ala Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Met Ala Val Tyr Tyr Cys
                85                  90                  95
Ala Arg Val Met Asn Tyr Tyr Gly Pro Gly Ser Ala Phe Asp Tyr Trp
            100                 105                 110
Gly Gln Gly Thr Leu Val Thr Val Ser Ser
        115                 120

<210> SEQ ID NO 46
<211> LENGTH: 499
<212> TYPE: PRT
<213> ORGANISM: Homo sapiens
<220> FEATURE:
<223> OTHER INFORMATION: PA21-G3 Heavy Chain

<400> SEQUENCE: 46

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ser Gly Ile Ser Gly Asp Ala Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Met Ala Val Tyr Tyr Cys
                85                  90                  95
Ala Arg Val Met Asn Tyr Tyr Gly Pro Gly Ser Ala Phe Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Cys Ser Arg Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175

-continued

```
Ala Val Leu Gln Ser Ser Gly Leu Tyr Ser Leu Ser Ser Val Val Thr
            180                 185                 190

Val Pro Ser Ser Leu Gly Thr Gln Thr Tyr Thr Cys Asn Val Asn
        195                 200                 205

His Lys Pro Ser Asn Thr Lys Val Asp Lys Arg Val Glu Leu Lys Thr
    210                 215                 220

Pro Leu Gly Asp Thr Thr His Thr Cys Pro Arg Cys Pro Glu Pro Lys
225                 230                 235                 240

Ser Cys Asp Thr Pro Pro Pro Cys Pro Arg Cys Pro Glu Pro Lys Ser
                245                 250                 255

Cys Asp Thr Pro Pro Pro Cys Pro Arg Cys Pro Glu Pro Lys Ser Cys
            260                 265                 270

Asp Thr Pro Pro Pro Cys Pro Arg Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Gln Phe Lys Trp Tyr Val Asp Gly Val Glu Val
                325                 330                 335

His Asn Ala Lys Thr Lys Pro Arg Glu Glu Gln Tyr Asn Ser Thr Phe
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Thr Lys Gly Gln Pro Arg Glu Pro Gln Val
385                 390                 395                 400

Tyr Thr Leu Pro Pro Ser Arg Glu Glu Met Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Ser Gly Gln Pro Glu Asn Asn Tyr Asn Thr Thr Pro Pro
        435                 440                 445

Met Leu Asp Ser Asp Gly Ser Phe Phe Leu Tyr Ser Lys Leu Thr Val
    450                 455                 460

Asp Lys Ser Arg Trp Gln Gln Gly Asn Ile Phe Ser Cys Ser Val Met
465                 470                 475                 480

His Glu Ala Leu His Asn Arg Phe Thr Gln Lys Ser Leu Ser Leu Ser
                485                 490                 495

Pro Gly Lys

<210> SEQ ID NO 47
<211> LENGTH: 11
<212> TYPE: PRT
<213> ORGANISM: Homo sapiens
<220> FEATURE:
<223> OTHER INFORMATION: PA21-G3 Light Chain CDR1

<400> SEQUENCE: 47

Arg Ala Ser Gln Ser Ile Ser Ser Tyr Leu Asn
1               5                   10

<210> SEQ ID NO 48
<211> LENGTH: 7
<212> TYPE: PRT
```

<213> ORGANISM: Homo sapiens
<220> FEATURE:
<223> OTHER INFORMATION: PA21-G3 Light Chain CDR2

<400> SEQUENCE: 48

Ala Ala Ser Ser Leu Gln Ser
1               5

<210> SEQ ID NO 49
<211> LENGTH: 9
<212> TYPE: PRT
<213> ORGANISM: Homo sapiens
<220> FEATURE:
<223> OTHER INFORMATION: PA21-G3 Light Chain CDR3

<400> SEQUENCE: 49

Gln Gln Ser Tyr Ser Thr Pro Ile Thr
1               5

<210> SEQ ID NO 50
<211> LENGTH: 108
<212> TYPE: PRT
<213> ORGANISM: Homo sapiens
<220> FEATURE:
<223> OTHER INFORMATION: PA21-G3 Light Chain Variable Domain

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg
            100                 105

<210> SEQ ID NO 51
<211> LENGTH: 214
<212> TYPE: PRT
<213> ORGANISM: Homo sapiens
<220> FEATURE:
<223> OTHER INFORMATION: PA21-G3 Light Chain

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile

```
                    85                  90                  95
Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 5
<212> TYPE: PRT
<213> ORGANISM: Homo sapiens
<220> FEATURE:
<223> OTHER INFORMATION: PA27-G3 Heavy Chain CDR1

<400> SEQUENCE: 52

Lys Tyr Gly Met Ser
1               5

<210> SEQ ID NO 53
<211> LENGTH: 17
<212> TYPE: PRT
<213> ORGANISM: Homo sapiens
<220> FEATURE:
<223> OTHER INFORMATION: PA27-G3 Heavy Chain CDR2

<400> SEQUENCE: 53

Thr Ile Ser Gly Ser Gly Phe Thr Thr Tyr Tyr Ala Asp Ser Val Lys
1               5                   10                  15

Gly

<210> SEQ ID NO 54
<211> LENGTH: 11
<212> TYPE: PRT
<213> ORGANISM: Homo sapiens
<220> FEATURE:
<223> OTHER INFORMATION: PA27-G3 Heavy Chain CDR3

<400> SEQUENCE: 54

Asp Gly Trp Asp Tyr Glu Asp Phe Phe Gly Ser
1               5                   10

<210> SEQ ID NO 55
<211> LENGTH: 120
<212> TYPE: PRT
<213> ORGANISM: Homo sapiens
<220> FEATURE:
<223> OTHER INFORMATION: PA27-G3 Heavy Chain Variable Domain

<400> SEQUENCE: 55

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Lys Tyr
            20                  25                  30

Gly Met Ser Trp Val Arg Gln Ala Pro Gly Lys Gly Leu Glu Trp Val
        35                  40                  45

Ser Thr Ile Ser Gly Ser Gly Phe Thr Thr Tyr Tyr Ala Asp Ser Val
    50                  55                  60

Lys Gly Arg Phe Thr Ile Ser Arg Asp Asp Phe Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asp Tyr Glu Asp Phe Phe Gly Ser Trp Gly Gln
            100                 105                 110

Gly Thr Leu Val Thr Val Ser Ser
            115                 120

<210> SEQ ID NO 56
<211> LENGTH: 497
<212> TYPE: PRT
<213> ORGANISM: Homo sapiens
<220> FEATURE:
<223> OTHER INFORMATION: PA27-G3 Heavy Chain

<400> SEQUENCE: 56

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Gly Met Ser Trp Val Arg Gln Ala Pro Gly Lys Gly Leu Glu Trp Val
        35                  40                  45

Ser Thr Ile Ser Gly Ser Gly Phe Thr Thr Tyr Tyr Ala Asp Ser Val
    50                  55                  60

Lys Gly Arg Phe Thr Ile Ser Arg Asp Asp Phe Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asp Tyr Glu Asp Phe Phe Gly Ser Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Thr Cys Asn Val Asn His Lys
        195                 200                 205

Pro Ser Asn Thr Lys Val Asp Lys Arg Val Glu Leu Lys Thr Pro Leu
    210                 215                 220

Gly Asp Thr Thr His Thr Cys Pro Arg Cys Pro Glu Pro Lys Ser Cys
225                 230                 235                 240

Asp Thr Pro Pro Pro Cys Pro Arg Cys Pro Glu Pro Lys Ser Cys Asp
                245                 250                 255
```

```
Thr Pro Pro Pro Cys Pro Arg Cys Pro Glu Pro Lys Ser Cys Asp Thr
                260                 265                 270

Pro Pro Pro Cys Pro Arg Cys Pro Ala Pro Glu Leu Leu Gly Gly Pro
            275                 280                 285

Ser Val Phe Leu Phe Pro Pro Lys Pro Lys Asp Thr Leu Met Ile Ser
        290                 295                 300

Arg Thr Pro Glu Val Thr Cys Val Val Val Asp Val Ser His Glu Asp
305                 310                 315                 320

Pro Glu Val Gln Phe Lys Trp Tyr Val Asp Gly Val Glu Val His Asn
                325                 330                 335

Ala Lys Thr Lys Pro Arg Glu Glu Gln Tyr Asn Ser Thr Phe Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Thr Lys Gly Gln Pro Arg Glu Pro Gln Val Tyr Thr
385                 390                 395                 400

Leu Pro Pro Ser Arg Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Ser Gly Gln Pro Glu Asn Asn Tyr Asn Thr Thr Pro Pro Met Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Ile Phe Ser Cys Ser Val Met His Glu
465                 470                 475                 480

Ala Leu His Asn Arg Phe Thr Gln Lys Ser Leu Ser Leu Ser Pro Gly
                485                 490                 495

Lys

<210> SEQ ID NO 57
<211> LENGTH: 11
<212> TYPE: PRT
<213> ORGANISM: Homo sapiens
<220> FEATURE:
<223> OTHER INFORMATION: PA27-G3 Light Chain CDR1

<400> SEQUENCE: 57

Arg Ala Ser Gln Ser Ile Ser Ser Tyr Leu Asn
1               5                   10

<210> SEQ ID NO 58
<211> LENGTH: 7
<212> TYPE: PRT
<213> ORGANISM: Homo sapiens
<220> FEATURE:
<223> OTHER INFORMATION: PA27-G3 Light Chain CDR2

<400> SEQUENCE: 58

Ala Ala Ser Ser Leu Gln Ser
1               5

<210> SEQ ID NO 59
<211> LENGTH: 9
<212> TYPE: PRT
<213> ORGANISM: Homo sapiens
```

<220> FEATURE:
<223> OTHER INFORMATION: PA27-G3 Light Chain CDR3

<400> SEQUENCE: 59

Gln Gln Ser Tyr Ala Phe Pro Tyr Thr
1               5

<210> SEQ ID NO 60
<211> LENGTH: 108
<212> TYPE: PRT
<213> ORGANISM: Homo sapiens
<220> FEATURE:
<223> OTHER INFORMATION: PA27-G3 Light Chain Variable Domain

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Thr Asn Leu Gln Pro
65                  70                  75                  80

Glu Asp Phe Gly Thr Tyr Tyr Cys Gln Gln Ser Tyr Ala Phe Pro Tyr
                85                  90                  95

Thr Phe Gly Gln Gly Thr Arg Leu Glu Ile Lys Arg
            100                 105

<210> SEQ ID NO 61
<211> LENGTH: 214
<212> TYPE: PRT
<213> ORGANISM: Homo sapiens
<220> FEATURE:
<223> OTHER INFORMATION: PA27-G3 Light Chain

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Thr Asn Leu Gln Pro
65                  70                  75                  80

Glu Asp Phe Gly Thr Tyr Tyr Cys Gln Gln Ser Tyr Ala Phe Pro Tyr
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

-continued

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 62
<211> LENGTH: 5
<212> TYPE: PRT
<213> ORGANISM: Homo sapiens
<220> FEATURE:
<223> OTHER INFORMATION: PA32-G3 Heavy Chain CDR1

<400> SEQUENCE: 62

Asp Tyr Tyr Met Asp
1               5

<210> SEQ ID NO 63
<211> LENGTH: 17
<212> TYPE: PRT
<213> ORGANISM: Homo sapiens
<220> FEATURE:
<223> OTHER INFORMATION: PA32-G3 Heavy Chain CDR2

<400> SEQUENCE: 63

Ser Ile Lys Ala Asp Gly Ser Glu Thr His Tyr Val Asp Ser Val Lys
1               5                   10                  15
Gly

<210> SEQ ID NO 64
<211> LENGTH: 8
<212> TYPE: PRT
<213> ORGANISM: Homo sapiens
<220> FEATURE:
<223> OTHER INFORMATION: PA32-G3 Heavy Chain CDR3

<400> SEQUENCE: 64

Asp Pro Gly Arg Arg Phe Asp Tyr
1               5

<210> SEQ ID NO 65
<211> LENGTH: 117
<212> TYPE: PRT
<213> ORGANISM: Homo sapiens
<220> FEATURE:
<223> OTHER INFORMATION: PA32-G3 Heavy Chain Variable Domain

<400> SEQUENCE: 65

Glu Val Gln Leu Val Glu Thr Gly Gly Gly Leu Ala Gln Pro Gly Gly
1               5                   10                  15
Ser Leu Arg Leu Ser Cys Ala Ala Ser Gly Phe Ile Phe Ser Asp Tyr
            20                  25                  30
Tyr Met Asp Trp Val Arg Gln Ala Pro Gly Lys Gly Pro Glu Trp Val
        35                  40                  45
Ala Ser Ile Lys Ala Asp Gly Ser Glu Thr His Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Val Glu Asp Thr Ala Val Tyr Tyr Cys
```

```
                 85                  90                  95
Gly Arg Asp Pro Gly Arg Arg Phe Asp Tyr Trp Gly Gln Gly Thr Leu
                100                 105                 110
Val Thr Val Ser Ser
            115

<210> SEQ ID NO 66
<211> LENGTH: 494
<212> TYPE: PRT
<213> ORGANISM: Homo sapiens
<220> FEATURE:
<223> OTHER INFORMATION: PA32-G3 Heavy Chain

<400> SEQUENCE: 66

Glu Val Gln Leu Val Glu Thr Gly Gly Gly Leu Ala Gln Pro Gly Gly
1               5                   10                  15

Ser Leu Arg Leu Ser Cys Ala Ala Ser Gly Phe Ile Phe Ser Asp Tyr
                20                  25                  30

Tyr Met Asp Trp Val Arg Gln Ala Pro Gly Lys Gly Pro Glu Trp Val
            35                  40                  45

Ala Ser Ile Lys Ala Asp Gly Ser Glu Thr His Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Gly Arg Asp Pro Gly Arg Arg Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Thr Cys Asn Val Asn His Lys Pro Ser Asn
        195                 200                 205

Thr Lys Val Asp Lys Arg Val Glu Leu Lys Thr Pro Leu Gly Asp Thr
    210                 215                 220

Thr His Thr Cys Pro Arg Cys Pro Glu Pro Lys Ser Cys Asp Thr Pro
225                 230                 235                 240

Pro Pro Cys Pro Arg Cys Pro Glu Pro Lys Ser Cys Asp Thr Pro Pro
                245                 250                 255

Pro Cys Pro Arg Cys Pro Glu Pro Lys Ser Cys Asp Thr Pro Pro Pro
            260                 265                 270

Cys Pro Arg Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Gln Phe Lys Trp Tyr Val Asp Gly Val Glu Val His Asn Ala Lys Thr
```

```
              325                 330                 335
Lys Pro Arg Glu Glu Gln Tyr Asn Ser Thr Phe Arg Val Val Ser Val
            340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
            370                 375                 380

Lys Thr Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Ser Gly
                420                 425                 430

Gln Pro Glu Asn Asn Tyr Asn Thr Thr Pro Pro Met Leu Asp Ser Asp
                435                 440                 445

Gly Ser Phe Phe Leu Tyr Ser Lys Leu Thr Val Asp Lys Ser Arg Trp
450                 455                 460

Gln Gln Gly Asn Ile Phe Ser Cys Ser Val Met His Glu Ala Leu His
465                 470                 475                 480

Asn Arg Phe Thr Gln Lys Ser Leu Ser Leu Ser Pro Gly Lys
                485                 490

<210> SEQ ID NO 67
<211> LENGTH: 11
<212> TYPE: PRT
<213> ORGANISM: Homo sapiens
<220> FEATURE:
<223> OTHER INFORMATION: PA32-G3 Light Chain CDR1

<400> SEQUENCE: 67

Arg Ala Ser Gln Ser Ile Ser Ser Tyr Leu Asn
1               5                   10

<210> SEQ ID NO 68
<211> LENGTH: 7
<212> TYPE: PRT
<213> ORGANISM: Homo sapiens
<220> FEATURE:
<223> OTHER INFORMATION: PA32-G3 Light Chain CDR2

<400> SEQUENCE: 68

Ala Ala Ser Ser Leu Gln Ser
1               5

<210> SEQ ID NO 69
<211> LENGTH: 9
<212> TYPE: PRT
<213> ORGANISM: Homo sapiens
<220> FEATURE:
<223> OTHER INFORMATION: PA32-G3 Light Chain CDR3

<400> SEQUENCE: 69

Gln Gln Ser Tyr Ser Thr Pro Tyr Thr
1               5

<210> SEQ ID NO 70
<211> LENGTH: 108
<212> TYPE: PRT
<213> ORGANISM: Homo sapiens
<220> FEATURE:
<223> OTHER INFORMATION: PA32-G3 Light Chain Variable Domain
```

<400> SEQUENCE: 70

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg
            100                 105

<210> SEQ ID NO 71
<211> LENGTH: 214
<212> TYPE: PRT
<213> ORGANISM: Homo sapiens
<220> FEATURE:
<223> OTHER INFORMATION: PA32-G3 Light Chain

<400> SEQUENCE: 71

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 5
<212> TYPE: PRT

<213> ORGANISM: Homo sapiens
<220> FEATURE:
<223> OTHER INFORMATION: PA37-G3 Heavy Chain CDR1

<400> SEQUENCE: 72

Ser Tyr Ala Met Asn
1               5

<210> SEQ ID NO 73
<211> LENGTH: 17
<212> TYPE: PRT
<213> ORGANISM: Homo sapiens
<220> FEATURE:
<223> OTHER INFORMATION: PA37-G3 Heavy Chain CDR2

<400> SEQUENCE: 73

Ala Ile Ser Gly Ser Gly Asp Ile Thr His Tyr Ala Asp Ser Val Lys
1               5                   10                  15

Gly

<210> SEQ ID NO 74
<211> LENGTH: 12
<212> TYPE: PRT
<213> ORGANISM: Homo sapiens
<220> FEATURE:
<223> OTHER INFORMATION: PA37-G3 Heavy Chain CDR3

<400> SEQUENCE: 74

Gly Pro Trp Leu Ala Pro Gly Gly Trp Phe Asp Pro
1               5                   10

<210> SEQ ID NO 75
<211> LENGTH: 121
<212> TYPE: PRT
<213> ORGANISM: Homo sapiens
<220> FEATURE:
<223> OTHER INFORMATION: PA37-G3 Heavy Chain Variable Domain

<400> SEQUENCE: 75

Glu Val Gln Leu Leu Glu Ser Gly Gly Gly Leu Val Gln Pro Gly Gly
1               5                   10                  15

Ser Arg Arg Leu Ser Cys Ala Thr Ser Gly Leu Ser Phe Ser Ser Tyr
                20                  25                  30

Ala Met Asn Trp Val Arg Gln Ala Pro Gly Lys Gly Leu Glu Trp Val
            35                  40                  45

Ser Ala Ile Ser Gly Ser Gly Asp Ile Thr His Tyr Ala Asp Ser Val
        50                  55                  60

Lys Gly Arg Leu Thr Ile Ser Arg Asp Asn Ser Lys Asn Thr Val Tyr
65                  70                  75                  80

Leu Gln Met Asn Ser Leu Arg Gly Glu Asp Thr Ala Val Tyr Tyr Cys
                85                  90                  95

Ala Lys Gly Pro Trp Leu Ala Pro Gly Gly Trp Phe Asp Pro Trp Gly
            100                 105                 110

Gln Gly Thr Leu Val Thr Val Ser Ser
        115                 120

<210> SEQ ID NO 76
<211> LENGTH: 498
<212> TYPE: PRT
<213> ORGANISM: Homo sapiens
<220> FEATURE:
<223> OTHER INFORMATION: PA37-G3 Heavy Chain

```
<400> SEQUENCE: 76

Glu Val Gln Leu Leu Glu Ser Gly Gly Gly Leu Val Gln Pro Gly Gly
1               5                   10                  15

Ser Arg Arg Leu Ser Cys Ala Thr Ser Gly Leu Ser Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Asp Ile Thr His Tyr Ala Asp Ser Val
    50                  55                  60

Lys Gly Arg Leu Thr Ile Ser Arg Asp Asn Ser Lys Asn Thr Val Tyr
65                  70                  75                  80

Leu Gln Met Asn Ser Leu Arg Gly Glu Asp Thr Ala Val Tyr Tyr Cys
                85                  90                  95

Ala Lys Gly Pro Trp Leu Ala Pro Gly Gly Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asn His
        195                 200                 205

Lys Pro Ser Asn Thr Lys Val Asp Lys Arg Val Glu Leu Lys Thr Pro
    210                 215                 220

Leu Gly Asp Thr Thr His Thr Cys Pro Arg Cys Pro Glu Pro Lys Ser
225                 230                 235                 240

Cys Asp Thr Pro Pro Pro Cys Pro Arg Cys Pro Glu Pro Lys Ser Cys
                245                 250                 255

Asp Thr Pro Pro Pro Cys Pro Arg Cys Pro Glu Pro Lys Ser Cys Asp
            260                 265                 270

Thr Pro Pro Pro Cys Pro Arg Cys Pro Ala Pro Glu Leu Leu Gly Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Gln Phe Lys Trp Tyr Val Asp Gly Val Glu Val His
                325                 330                 335

Asn Ala Lys Thr Lys Pro Arg Glu Glu Gln Tyr Asn Ser Thr Phe Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Thr Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415
```

```
Thr Cys Leu Val Lys Gly Phe Tyr Pro Ser Asp Ile Ala Val Glu Trp
        420                 425                 430

Glu Ser Ser Gly Gln Pro Glu Asn Asn Tyr Asn Thr Thr Pro Pro Met
            435                 440                 445

Leu Asp Ser Asp Gly Ser Phe Phe Leu Tyr Ser Lys Leu Thr Val Asp
450                 455                 460

Lys Ser Arg Trp Gln Gln Gly Asn Ile Phe Ser Cys Ser Val Met His
465                 470                 475                 480

Glu Ala Leu His Asn Arg Phe Thr Gln Lys Ser Leu Ser Leu Ser Pro
                485                 490                 495

Gly Lys

<210> SEQ ID NO 77
<211> LENGTH: 11
<212> TYPE: PRT
<213> ORGANISM: Homo sapiens
<220> FEATURE:
<223> OTHER INFORMATION: PA37-G3 Light Chain CDR1

<400> SEQUENCE: 77

Arg Ala Ser Gln Ser Ile Ser Ser Tyr Leu Asn
1               5                   10

<210> SEQ ID NO 78
<211> LENGTH: 7
<212> TYPE: PRT
<213> ORGANISM: Homo sapiens
<220> FEATURE:
<223> OTHER INFORMATION: PA37-G3 Light Chain CDR2

<400> SEQUENCE: 78

Ala Ala Ser Ser Leu Gln Ser
1               5

<210> SEQ ID NO 79
<211> LENGTH: 9
<212> TYPE: PRT
<213> ORGANISM: Homo sapiens
<220> FEATURE:
<223> OTHER INFORMATION: PA37-G3 Light Chain CDR3

<400> SEQUENCE: 79

Gln Gln Ser Tyr Ser Thr Pro Tyr Thr
1               5

<210> SEQ ID NO 80
<211> LENGTH: 108
<212> TYPE: PRT
<213> ORGANISM: Homo sapiens
<220> FEATURE:
<223> OTHER INFORMATION: PA37-G3 Light Chain Variable Domain

<400> SEQUENCE: 80

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60
```

-continued

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu Ile Lys Arg
            100                 105
```

<210> SEQ ID NO 81
<211> LENGTH: 214
<212> TYPE: PRT
<213> ORGANISM: Homo sapiens
<220> FEATURE:
<223> OTHER INFORMATION: PA37-G3 Light Chain

<400> SEQUENCE: 81

```
Ala Ile Arg Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 82
<211> LENGTH: 21
<212> TYPE: PRT
<213> ORGANISM: Staphylococcus aureus
<220> FEATURE:
<223> OTHER INFORMATION: Antigenic Peptide #1

<400> SEQUENCE: 82

```
Gly Glu Ala Lys Lys Leu Asn Glu Ser Gln Ala Pro Lys Ala Asp Asn
  1               5                  10                  15

Asn Phe Asn Lys Glu
             20
```

<210> SEQ ID NO 83

-continued

```
<211> LENGTH: 16
<212> TYPE: PRT
<213> ORGANISM: Staphylococcus aureus
<220> FEATURE:
<223> OTHER INFORMATION: Antigenic Peptide #2

<400> SEQUENCE: 83

Pro Asn Leu Asn Glu Glu Gln Arg Asn Gly Phe Ile Gln Ser Leu Lys
1               5                   10                  15

<210> SEQ ID NO 84
<211> LENGTH: 21
<212> TYPE: PRT
<213> ORGANISM: Staphylococcus aureus
<220> FEATURE:
<223> OTHER INFORMATION: Antigenic Peptide #3

<400> SEQUENCE: 84

Ala Glu Ala Lys Lys Leu Asn Asp Ala Gln Ala Pro Lys Ala Asp Asn
1               5                   10                  15

Lys Phe Asn Lys Glu
            20

<210> SEQ ID NO 85
<211> LENGTH: 20
<212> TYPE: PRT
<213> ORGANISM: Staphylococcus aureus
<220> FEATURE:
<223> OTHER INFORMATION: Antigenic Peptide #4

<400> SEQUENCE: 85

Lys Glu Ile Leu Ala Glu Ala Lys Lys Leu Asn Asp Ala Gln Ala Pro
1               5                   10                  15

Lys Glu Glu Asp
            20

<210> SEQ ID NO 86
<211> LENGTH: 520
<212> TYPE: PRT
<213> ORGANISM: Staphylococcus aureus
<220> FEATURE:
<223> OTHER INFORMATION: Protein A

<400> SEQUENCE: 86

Met Met Thr Leu Gln Ile His Thr Gly Gly Ile Asn Leu Lys Lys Lys
1               5                   10                  15

Asn Ile Tyr Ser Ile Arg Lys Leu Gly Val Gly Ile Ala Ser Val Thr
            20                  25                  30

Leu Gly Thr Leu Leu Ile Ser Gly Gly Val Thr Pro Ala Ala Asn Ala
        35                  40                  45

Ala Gln His Asp Glu Ala Gln Gln Asn Ala Phe Tyr Gln Val Leu Asn
    50                  55                  60

Met Pro Asn Leu Asn Ala Asp Gln Arg Asn Gly Phe Ile Gln Ser Leu
65                  70                  75                  80

Lys Asp Asp Pro Ser Gln Ser Ala Asn Val Leu Gly Glu Ala Gln Lys
                85                  90                  95

Leu Asn Asp Ser Gln Ala Pro Lys Ala Asp Ala Gln Gln Asn Asn Phe
            100                 105                 110

Asn Lys Asp Gln Gln Ser Ala Phe Tyr Glu Ile Leu Asn Met Pro Asn
        115                 120                 125

Leu Asn Glu Ala Gln Arg Asn Gly Phe Ile Gln Ser Leu Lys Asp Asp
    130                 135                 140
```

-continued

```
Pro Ser Gln Ser Thr Asn Val Leu Gly Glu Ala Lys Lys Leu Asn Glu
145                 150                 155                 160

Ser Gln Ala Pro Lys Ala Asp Asn Asn Phe Asn Lys Glu Gln Gln Asn
            165                 170                 175

Ala Phe Tyr Glu Ile Leu Asn Met Pro Asn Leu Asn Glu Glu Gln Arg
            180                 185                 190

Asn Gly Phe Ile Gln Ser Leu Lys Asp Asp Pro Ser Gln Ser Ala Asn
            195                 200                 205

Leu Leu Ser Glu Ala Lys Lys Leu Asn Glu Ser Gln Ala Pro Lys Ala
            210                 215                 220

Asp Asn Lys Phe Asn Lys Glu Gln Gln Asn Ala Phe Tyr Glu Ile Leu
225                 230                 235                 240

His Leu Pro Asn Leu Asn Glu Glu Gln Arg Asn Gly Phe Ile Gln Ser
                245                 250                 255

Leu Lys Asp Asp Pro Ser Gln Ser Ala Asn Leu Leu Ala Glu Ala Lys
            260                 265                 270

Lys Leu Asn Asp Ala Gln Ala Pro Lys Ala Asp Asn Lys Phe Asn Lys
            275                 280                 285

Glu Gln Gln Asn Ala Phe Tyr Glu Ile Leu His Leu Pro Asn Leu Thr
290                 295                 300

Glu Glu Gln Arg Asn Gly Phe Ile Gln Ser Leu Lys Asp Asp Pro Ser
305                 310                 315                 320

Val Ser Lys Glu Ile Leu Ala Glu Ala Lys Lys Leu Asn Asp Ala Gln
            325                 330                 335

Ala Pro Lys Glu Glu Asp Asn Asn Lys Pro Gly Lys Glu Asp Asn Asn
            340                 345                 350

Lys Pro Gly Lys Glu Asp Asn Asn Lys Pro Gly Lys Glu Asp Asn Asn
            355                 360                 365

Lys Pro Gly Lys Glu Asp Gly Asn Lys Pro Gly Lys Glu Asp Asn Lys
            370                 375                 380

Lys Pro Gly Lys Glu Asp Gly Asn Lys Pro Gly Lys Glu Asp Asn Lys
385                 390                 395                 400

Lys Pro Gly Lys Glu Asp Gly Asn Lys Pro Gly Lys Glu Asp Gly Asn
            405                 410                 415

Lys Pro Gly Lys Glu Asp Gly Asn Gly Val His Val Val Lys Pro Gly
            420                 425                 430

Asp Thr Val Asn Asp Ile Ala Lys Ala Asn Gly Thr Thr Ala Asp Lys
            435                 440                 445

Ile Ala Ala Asp Asn Lys Leu Ala Asp Lys Asn Met Ile Lys Pro Gly
            450                 455                 460

Gln Glu Leu Val Val Asp Lys Lys Gln Pro Ala Asn His Ala Asp Ala
465                 470                 475                 480

Asn Lys Ala Gln Ala Leu Pro Glu Thr Gly Glu Glu Asn Pro Phe Ile
            485                 490                 495

Gly Thr Thr Val Phe Gly Gly Leu Ser Leu Ala Leu Gly Ala Ala Leu
            500                 505                 510

Leu Ala Gly Arg Arg Arg Glu Leu
            515                 520
```